US011805802B2

(12) United States Patent
Stahl et al.

(10) Patent No.: US 11,805,802 B2
(45) Date of Patent: Nov. 7, 2023

(54) NICOTINE POUCH COMPOSITION

(71) Applicant: PHILIP MORRIS PRODUCTS S.A., Neuchatel (CH)

(72) Inventors: My Ly Lao Stahl, Vejle Ost (DK); Heidi Ziegler Bruun, Vejle Ost (DK); Bruno Provstgaard Nielsen, Vejle Ost (DK); Jesper Neergaard, Aabenraa (DK); Bine Hare Jakobsen, Ry (DK)

(73) Assignee: PHILIP MORRIS PRODUCTS S.A., Neuchatel (CH)

( * ) Notice: Subject to any disclaimer, the term of this patent is extended or adjusted under 35 U.S.C. 154(b) by 0 days.

(21) Appl. No.: 17/048,054

(22) PCT Filed: Jun. 5, 2020

(86) PCT No.: PCT/DK2020/050160
§ 371 (c)(1),
(2) Date: Oct. 15, 2020

(87) PCT Pub. No.: WO2020/244722
PCT Pub. Date: Dec. 10, 2020

(65) Prior Publication Data

US 2021/0307375 A1    Oct. 7, 2021

(30) Foreign Application Priority Data

Jun. 7, 2019    (DK) .............................. PA201900698
Sep. 30, 2019   (DK) .............................. PA201970610
Sep. 30, 2019   (DK) .............................. PA201970611
Sep. 30, 2019   (DK) .............................. PA201970612

(51) Int. Cl.
    *A24B 15/16*        (2020.01)
    *A24B 13/00*        (2006.01)

(52) U.S. Cl.
    CPC .............. *A24B 15/16* (2013.01); *A24B 13/00* (2013.01)

(58) Field of Classification Search
    CPC ......... A24B 15/16; A24B 15/00; A24B 15/30; A24B 15/302; A24B 15/32; A24B 15/40; A24B 15/403; A24B 15/42; A24B 13/00
    See application file for complete search history.

(56) References Cited

U.S. PATENT DOCUMENTS

| 5,167,244 | A | 12/1992 | Kjerstad | |
| 8,863,755 | B2* | 10/2014 | Zhuang | A24B 15/183 131/352 |
| 9,402,809 | B2* | 8/2016 | Axelsson | A61K 9/009 |
| 11,096,412 | B2 | 8/2021 | Stahl et al. | |
| 2005/0034738 | A1* | 2/2005 | Whalen | A24B 15/16 131/352 |
| 2005/0053665 | A1* | 3/2005 | Ek | A61P 25/16 424/488 |
| 2008/0302682 | A1 | 12/2008 | Engstrom et al. | |
| 2011/0214681 | A1 | 9/2011 | Axelsson et al. | |
| 2012/0247492 | A1* | 10/2012 | Kobal | A24B 15/18 131/290 |
| 2013/0078308 | A1 | 3/2013 | Hashimoto et al. | |
| 2013/0108558 | A1 | 5/2013 | Andersen | |
| 2013/0152953 | A1 | 6/2013 | Mua et al. | |
| 2013/0251779 | A1 | 9/2013 | Svandal et al. | |
| 2015/0020818 | A1 | 1/2015 | Gao et al. | |
| 2015/0068545 | A1 | 3/2015 | Moldoveanu et al. | |
| 2015/0096576 | A1 | 4/2015 | Gao et al. | |
| 2016/0000140 | A1 | 1/2016 | Sebastian et al. | |
| 2016/0165953 | A1 | 6/2016 | Goode, Jr. | |
| 2016/0192703 | A1 | 7/2016 | Sebastian et al. | |
| 2017/0318858 | A1 | 11/2017 | Hodin et al. | |
| 2018/0271139 | A1 | 9/2018 | Aspgren et al. | |
| 2019/0037909 | A1 | 2/2019 | Greenbaum et al. | |
| 2020/0297024 | A1 | 9/2020 | Bodin | |

FOREIGN PATENT DOCUMENTS

| CN | 101222915 A | 7/2008 |
| CN | 101272703 A | 9/2008 |
| CN | 101877975 A | 11/2010 |
| CN | 103491958   | 1/2014 |
| CN | 107205471 A | 9/2017 |
| CN | 107319629 A | 11/2017 |
| EP | 2692254 A1  | 2/2014 |
| EP | 3087852 A1  | 11/2016 |
| EP | 3491940 A1  | 6/2019 |
| GB | 673587 A    | 6/1952 |
| IN | 171981 B    | 3/1993 |
| NO | 20170683 A1 | 10/2018 |
| WO | 2007084587 A2 | 7/2007 |

(Continued)

OTHER PUBLICATIONS

Wikipedia, "Sugar alcohol"; https://en.wikipedia.org/wiki/Sugar_alcohol; downloaded from Internet on Sep. 27, 2017.
Additional Search Report from Danish Patent and Trademark Office for Application No. PA 2019 70610 dated Jul. 30, 2020 (2 pages).
Additional Search Report from Danish Patent and Trademark Office for Application No. PA 2019 70612 dated Aug. 4, 2020 (2 pages).
Search Report from Danish Patent and Trademark Office for Application No. PA 2019 00698 dated Dec. 3, 2019 (1 page).
Search Report from Danish Patent and Trademark Office for Application No. PA 2019 70610 dated Feb. 5, 2020 (2 pages).
Search Report from Danish Patent and Trademark Office for Application No. PA 2019 70611 dated Jan. 24, 2020 (2 pages).
Search Report from Danish Patent and Trademark Office for Application No. PA2019 70612 dated Feb. 3, 2020 (2 pages).

(Continued)

*Primary Examiner* — Philip Y Louie
*Assistant Examiner* — Yana B Krinker
(74) *Attorney, Agent, or Firm* — Oblon, McClelland, Maier & Neustadt, L.L.P.

(57) ABSTRACT

A nicotine pouch composition is disclosed, the pouch composition includes at least one sugar alcohol, at least one water-insoluble fiber, water in an amount of 8-65% by weight of the composition, and nicotine. Also, an oral pouched nicotine product and a method for manufacturing an oral pouched product is disclosed.

22 Claims, No Drawings

(56) References Cited

FOREIGN PATENT DOCUMENTS

| | | | |
|---|---|---|---|
| WO | 2007104573 A2 | 9/2007 | |
| WO | 2008056135 A2 | 5/2008 | |
| WO | 2009010881 A2 | 1/2009 | |
| WO | 2010121619 A1 | 10/2010 | |
| WO | 2012134380 A1 | 10/2012 | |
| WO | 2013090366 A2 | 6/2013 | |
| WO | 2013152918 A1 | 10/2013 | |
| WO | 2015052282 A1 | 4/2015 | |
| WO | 2015067372 A1 | 5/2015 | |
| WO | WO-2015067372 A1 * | 5/2015 | ............. A24B 15/16 |
| WO | 2015193379 A1 | 12/2015 | |
| WO | 2016083463 A1 | 6/2016 | |
| WO | 2017153718 A1 | 9/2017 | |
| WO | 2018011470 A1 | 1/2018 | |
| WO | 2018126262 A2 | 7/2018 | |
| WO | 2018197454 A1 | 11/2018 | |
| WO | 2018233795 A1 | 12/2018 | |
| WO | 2019115778 A1 | 6/2019 | |
| WO | 2020157280 A1 | 8/2020 | |

OTHER PUBLICATIONS

International Search Report Application No. PCT/DK2020/050159; dated Aug. 12, 2020; 3 pages.
International Search Report Application No. PCT/DK2020/050160; dated Oct. 1, 2020; 3 pages.
International Search Report Application No. PCT/DK2020/050162; dated Oct. 2, 2020; 4 pages.
International Search Report Application No. PCT/DK2020/050163; dated Oct. 7, 2020; 4 pages.
Seidenberg, Andrew B., Olalekan A. Ayo-Yusuf, and Vaughan W. Rees. "Characteristics of American Snus" and Swedish Snus Products for Sale in Massachusetts, USA. Nicotine and Tobacco Research 20.2 (2018): 262-266.
Combined Chinese Office Action and Search Report dated Sep. 14, 2022 in Patent Application No. 202080041486.7 (with English language translation), 23 pages.
Extended European Search Report dated Feb. 9, 2023, in corresponding European Patent Application No. 22208954.2, 19 pages.
Anonymous: "Sugar alcohol", Wikipedia, Apr. 30, 2017, pp. 1-4, XP055425206, 4 pages Retrieved from the Inernet: URL:https://en.wikipedia.org/wiki/Sugar_alcohol [retrieved on Nov. 15, 2017].
Notice of Allowance and Search Report dated Aug. 10, 2023, in corresponding Chinese Patent Application No. 202080041486.7 (with English Translation).

* cited by examiner

NICOTINE POUCH COMPOSITION

FIELD OF THE INVENTION

The present invention related to a nicotine pouch composition, an oral pouched nicotine product, and a method of manufacturing an oral pouched product.

BACKGROUND OF THE INVENTION

Delivery of nicotine by smoking has many well-known drawbacks, in particular health related problems, such as inclusion of carcinogenic substances.

However, tobacco substitutes also suffer from disadvantages, such as inadequate relief of cravings for the user.

It is an object of one embodiment of the present invention to provide a nicotine containing pouch, e.g. as a tobacco substitute, which may solve the above problems.

A further challenge in the prior art is that the desired release of nicotine should be attractive to the user of the pouch from a user perspective.

Yet at further challenge in relation to the prior art may be that pouches as delivery vehicle for nicotine may be somewhat costly and thereby impose restrictions on the way pouches are designed in order to keep manufacturing costs in check.

SUMMARY OF THE INVENTION

The invention related to a nicotine pouch composition comprising
at least one sugar alcohol,
at least one water-insoluble fiber,
water in an amount of 8-65% by weight of the composition, and
nicotine.

An advantage of the invention may be that a surprisingly high mobility of the pouch composition is obtained. This facilitates an effective processing of the pouch composition, particularly in filling the pouch composition into pouches. Typically, when handing powdered compositions, flowability is used as a measure of the processability. However, when adding significant amounts of water to the sugar alcohol containing pouch composition, the pouch composition tends to agglomerate and the flowability is drastically reduced, possibly even to the point where it cannot be measured by conventional methods. Nevertheless, the present inventors unexpectedly found that the pouch composition was still processable in filling machinery into individual pouches. Thus, the present invention facilitates effective processing and thereby a cost-effective setup by avoiding e.g. filling of the pouches by hand or very complex, special designed filling machinery.

A further advantage of the invention is that a very attractive soft, moist, and moldable texture and mouthfeel is obtained due to a combination of sugar alcohol, water-insoluble fiber and water. The desirable texture and mouthfeel may be obtained while still being able to store manufactured pouches together in abutment e.g. in cans etc. without sticking too much together to result in ruptures of the pouches when being removed.

An even further advantage of the invention is that the combination of sugar alcohol, water-insoluble fiber and water provides not only an attractive mouthfeel but also a very attractive taste profile.

In an advantageous embodiment of the invention, the composition has a bulk density of at most 0.8 g/cm3, such as has a bulk density of at most 0.7 g/cm3, such as at most 0.6 g/cm3, such as at most 0.5 g/cm3.

The inventive use of a composition having a relatively low bulk density, will provide not only a good mouthfeel, but also an effective release from the pouch, due to the fact that a relatively low bulk density promotes effective salivation and thereby release of water-soluble ingredients of the composition. It is in particular noted that the low bulk density, in combination with the claimed water content, is attractive when improved user perception is desired.

An advantage of the above embodiment may be that a low-density composition may be obtained. Unexpectedly, the combination of water and sugar alcohols did not lead to a very dense, compact and un-processable pouch composition but allowed a relatively light and low-density composition.

In an advantageous embodiment of the invention, the composition has a bulk density between 0.2 g/cm3 and 0.8 g/cm3, such as between 0.3 g/cm3 and 0.7 g/cm3, such as between 0.3 g/cm3 and 0.6 g/cm3, such as between 0.4 and 0.5 g/cm3.

In an embodiment of the invention, the composition has a bulk density between 0.2 g/cm3 and 0.8 g/cm3, such as between 0.2 g/cm3 and 0.7 g/cm3, such as between 0.2 g/cm3 and 0.6 g/cm3, such as between 0.2 and 0.5 g/cm3.

In an embodiment of the invention, the composition has a bulk density between 0.2 g/cm3 and 0.8 g/cm3, such as between 0.3 g/cm3 and 0.8 g/cm3, such as between 0.4 g/cm3 and 0.8 g/cm3, such as between 0.5 and 0.8 g/cm3.

The inventive use of a composition having a relatively low bulk density, will provide not only a good mouthfeel, but also an effective release from the pouch, due to the fact that a relatively low bulk density promotes effective salivation and thereby release of water-soluble ingredients of the composition. It is in particular noted that the low bulk density, in combination with the claimed water content, is attractive when improved user perception is desired.

At the same time, a low density advantageously lowers the need for raw materials and thereby decreases production costs.

The density of the pouch composition may be affected by a number of parameters, particularly type(s) and amount(s) of sugar alcohol(s), type(s) and amount(s) of fiber(s), content of water, and processing hereunder mixing time. While varying the amount of e.g. water also affects mobility such that adding too much water results in a to compact and dense pouch formulation, selecting a fiber with higher water binding capacity may at least partly counteract a higher water content. Also, it was observed that excessive mixing could lead to a too compact and dense pouch composition.

In an advantageous embodiment of the invention, the nicotine is selected from the group consisting of a nicotine salt, nicotine free base, nicotine bound to an ion exchanger, such as an ion exchange resin, such as nicotine polacrilex resin, a nicotine inclusion complex or nicotine in any non-covalent binding; nicotine bound to zeolites; nicotine bound to cellulose, such as microcrystalline cellulose, or starch microspheres, and mixtures thereof.

One example of a combination of different types of nicotine is the combination of free-base nicotine mixed with polacrilex resin, where some nicotine is be bound to the ion exchange resin, whereas some nicotine remains unbound.

Free base nicotine includes nicotine mixed with sugar alcohols, modified Calcium carbonate, water-soluble fibers, ion exchange resin, and combinations thereof. Nicotine bound to modified Calcium carbonate is described in international patent application WO 2010/121619, hereby incorporated by reference.

In an advantageous embodiment of the invention, the nicotine comprises non-salt nicotine.

In an advantageous embodiment of the invention, the nicotine comprises nicotine free base.

A very significant advantage of the above embodiment may be that a long shelf life of the pouched product may be obtained, with a long-life taste and texture. Providing nicotine in the free base form allows facilitates obtaining a higher pH in the pouch composition, without using too much alkaline pH adjusting agent.

Thus, in the above embodiment, the amount of alkaline pH adjusting agent may be reduced without compromising the shelf life and long-life taste and texture.

In an advantageous embodiment, the nicotine comprises nicotine mixed with ion exchange resin.

In an advantageous embodiment of the invention the nicotine comprises free-base nicotine mixed with ion exchange resin in a weight ratio between the free-base nicotine and the ion exchange resin of 0.1 to 2.0, preferably from 0.5 to 2.0, and most preferred about 0.67 to 1.0.

In an embodiment of the invention the nicotine comprises free-base nicotine mixed with ion exchange resin in a weight ratio between the free-base nicotine and the ion exchange resin of 1:1 to about 1:10, preferably from 1:2 to 1:6, and most preferred about 1:4-1:5.

Here, a weight ratio refers to the ratio of the mass of the first component divided by the mass of the second component. The term mixing ratio may also be used.

Thus, in the above embodiment, the nicotine comprises free-base nicotine mixed with ion exchange resin in a weight ratio between the free-base nicotine and the ion exchange resin of 0.1 to about 1, preferably from 0.17 to 0.5, and most preferred about 0.2-0.25.

In an advantageous embodiment of the invention, the nicotine comprises a nicotine salt.

In an embodiment of the invention, the nicotine salt is selected from nicotine ascorbate, nicotine aspartate, nicotine benzoate, nicotine monotartrate, nicotine bitartrate, nicotine chloride (e.g., nicotine hydrochloride and nicotine dihydrochloride), nicotine citrate, nicotine fumarate, nicotine gensitate, nicotine lactate, nicotine mucate, nicotine laurate, nicotine levulinate, nicotine malate nicotine perchlorate, nicotine pyruvate, nicotine salicylate, nicotine sorbate, nicotine succinate, nicotine zinc chloride, nicotine sulfate, nicotine tosylate and hydrates thereof (e.g., nicotine zinc chloride monohydrate).

In an embodiment of the invention, the nicotine salt comprises or consists of nicotine bitartrate.

In an advantageous embodiment of the invention, the nicotine comprises nicotine bound to an ion exchange resin.

In an embodiment of the invention, the ion exchange resin is a polacrilex resin.

In an embodiment of the invention, the polacrilex resin is AMBERLITE®IRP64.

In an advantageous embodiment of the invention, the nicotine comprises synthetic nicotine.

In an embodiment of the invention, the pouch composition further comprises nicotine as a complex with an ion exchange resin, such as polacrilex resin.

An advantage of the above embodiment may be a sustained release component may be obtained due to the complex with nicotine and ion exchange resin.

In an embodiment of the invention, the pouch composition comprises free-base nicotine mixed with ion exchange resin combined with nicotine as a complex with an ion exchange resin, such as polacrilex resin.

In an embodiment the nicotine consists of free-base nicotine mixed with polacrilex resin.

In an embodiment of the invention, the nicotine comprises nicotine mixed with ion exchange resin, such as polacrilex resin, the nicotine pouch composition further comprises nicotine bound to an ion exchange resin, i.e. a nicotine ion exchange resin complex. Thus, the nicotine may be nicotine mixed with polacrilex resin, where some nicotine is bound to the ion exchange resin, whereas some nicotine remains unbound as free-base nicotine.

In an advantageous embodiment of the invention, the pouch composition comprises nicotine in an amount of at least 0.1% by weight, such as least 0.2% by weight of the pouch composition.

In an advantageous embodiment of the invention, the pouch composition comprises nicotine in an amount of 0.1 to 5.0% by weight of the pouch composition, such as 0.2 to 4.0% by weight of the pouch composition, such as 1.0 to 2.0% by weight of the pouch composition.

A release profile of nicotine may be obtained which both comprises a fast release period and a sustained release period.

In an embodiment, the fast release period may refer to the initial 120 seconds of the nicotine release profile, whereas the sustained release period may refer to the subsequent period of the release profile until end of experiment or end of use, such as a period from 2 minutes until 30 minutes after initiation of use.

In an advantageous embodiment of the invention, the pouch composition is adapted to release at least 15% by weight of the nicotine within a period of 120 seconds in contact with oral saliva, such as at least 20% by weight of the nicotine, such as at least 30% by weight of the nicotine, such as at least 40% by weight of the nicotine, when provided in a pouch and the release measured as described in example 3K.

In an embodiment of the invention, the pouch composition is adapted to release at least 50% by weight of the nicotine within a period of 120 seconds in contact with oral saliva, when provided in a pouch. Preferably, the release is measured as described in example 3K.

In an embodiment of the invention, the pouch composition is adapted to release at least 15% by weight of the nicotine within a period of 120 seconds, such as at least 20% by weight of the nicotine, such as at least 30% by weight of the nicotine, when provided in a pouch and exposed to the in vitro release experiment described in example 3L.

In an embodiment of the invention, the pouch composition is adapted to release at least 30% by weight of the nicotine within a period of 10 minutes in contact with oral saliva, such as at least 40% by weight of the nicotine, such as at least 50% by weight of the nicotine, such as at least 60% by weight of the nicotine, when provided in a pouch and the release measured as described in example 3K.

In an embodiment of the invention, the pouch composition is adapted to release at least 30% by weight of the nicotine within a period of 10 minutes, such as at least 40% by weight of the nicotine, such as at least 50% by weight of the nicotine, such as at least 60% by weight of the nicotine, when provided in a pouch and exposed to the in vitro release experiment described in example 3L.

Release rate describes the average release of nicotine per minute within a given period.

In an advantageous embodiment of the invention, the pouch composition provided in a pouch to the oral cavity have a release rate of nicotine of at least 0.2% per minute within the release period from 2 to 10 minutes, such as at least 0.3% per minute within the release period from 2 to 10 minutes, such as at least 0.4% per minute within the release period from 2 to 10 minutes, such as at least 0.5% per minute within the release period from 2 to 10 minutes.

The above release rate may be calculated based on release results measured as described in example 3K.

In an embodiment of the invention, the pouch composition provided in a pouch and exposed to the in vitro release experiment described in example 3L have a release rate of nicotine of at least 0.2% per minute within the release period of 2 to 60 minutes, such as at least 0.3% per minute within the release period of 2 to 60 minutes, such as at least 0.4% per minute within the release period of 2 to 60 minutes, such as at least 0.5% per minute within the release period of 2 to 60 minutes.

In an embodiment of the invention, the pouch composition provided in a pouch and exposed to the in vitro release experiment described in example 3L have a release rate of nicotine of at least 0.2% per minute within the release period of 2 to 30 minutes, such as at least 0.3% per minute within the release period of 2 to 30 minutes, such as at least 0.4% per minute within the release period of 2 to 30 minutes, such as at least 0.5% per minute within the release period of 2 to 30 minutes.

In an advantageous embodiment of the invention, the pouch composition provided in a pouch and exposed to the in vitro release experiment described in example 3L have a release rate of nicotine of at least 0.2% per minute within the release period of 2 to 10 minutes, such as at least 0.3% per minute within the release period of 2 to 10 minutes, such as at least 0.4% per minute within the release period of 2 to 10 minutes, such as at least 0.5% per minute within the release period of 2 to 10 minutes.

In an embodiment of the invention, the pouch composition provided in a pouch and exposed to the in vitro release experiment described in example 3L have a release rate of nicotine of at least 0.1 mg per minute within the release period of 2 to 60 minutes, such as at least 0.2 mg per minute within the release period of 2 to 60 minutes.

In an embodiment of the invention, the pouch composition provided in a pouch and exposed to the in vitro release experiment described in example 3L have a release rate of nicotine of at least 0.4 mg per minute within the release period of 2 to 10 minutes.

In an advantageous embodiment of the invention, the pouch composition further comprises a pH-regulating agent, such as a basic pH-regulating agent, such as a basic buffering agent.

An advantage of the above embodiment may be that a more effective uptake of nicotine may be obtained, especially when using a basic (alkaline) pH regulating agent.

Another advantage of the above embodiment may be that a desirable mouthfeel may be obtained during use.

While lower amounts of pH regulating agent may be applicable in embodiments, e.g. by avoiding the use of nicotine salts, such as nicotine bitartrate, it may still be desirable to further increase the pH by adding pH regulating agent.

In an advantageous embodiment of the invention, the pouch composition comprises an alkaline buffering agent.

In an embodiment of the invention, the pouch composition further comprises a combination of at least two pH-regulating agents, such as a combination of at least two basic pH-regulating agents, such as a combination of at least two basic buffering agents, such as a basic buffer pair.

As used herein, the term alkaline buffering agent is used interchangeable with basic buffering agent, i.e. alkaline is used in the sense of "basic" as opposed to acidic.

In an advantageous embodiment of the invention, the pouch composition comprises the pH-regulating agent in an amount of less than 6% by weight of the pouch composition, such as less than 5% by weight of the pouch composition, such as less than 4% by weight by weight of the pouch composition, such as less than 2% by weight by weight of the pouch composition, such as less than 1% by weight by weight of the pouch composition, such as free of pH-regulating agent.

In an embodiment of the invention, the pouch composition comprises pH-regulating agents in an amount of 0 to 6% by weight of the pouch composition, such as 0 to 5% by weight of the pouch composition, such as 0 to 4% by weight of the pouch composition, such as 0 to 3% by weight of the pouch composition, such as 0 to 2% by weight of the pouch composition such as 0 to 1% by weight of the pouch composition.

In an embodiment of the invention, the pouch composition comprises pH-regulating agents in an amount of 0.1 to 6% by weight of the pouch composition, such as in an amount of 0.1 to 5% by weight of the pouch composition, such as in an amount of 0.5 to 5% by weight of the pouch composition, such as in an amount of 0.5 to 4% by weight of the pouch composition, such as in an amount of 0.1 to 3% by weight of the pouch composition, such as in an amount of 0.1 to 2% by weight of the pouch composition, such as in an amount of 0.1 to 1% by weight of the pouch composition.

In an embodiment of the invention, the pouch composition comprises pH regulating agent, e.g. in an amount of 0.01 and 15% by weight of the pouch composition.

In an advantageous embodiment of the invention, the pouch composition comprises pH regulating agent in an amount between 0.01 and 15% by weight of the pouch composition, such as between 0.5 and 10% by weight of the pouch composition, such as between 1 and 10% by weight of the pouch composition, such as between 5 and 10% by weight of the pouch composition.

In an advantageous embodiment of the invention, the pouch composition is adapted to give a pH of at least 8.0, such as a pH of at least 9.0, when 2.0 gram of pouch composition is added to 20 mL of 0.02 M potassium dihydrogen phosphate-buffer (pH adjusted to 7.4).

In an advantageous embodiment of the invention, the pouch composition is adapted to give a pH of at least 8.2, such as a pH of at least 8.5, such as a pH of at least 8.7, when 2.0 gram of pouch composition is added to 20 mL of 0.02 M potassium dihydrogen phosphate-buffer (pH adjusted to 7.4).

An advantage of the above embodiment may be that a relatively effective uptake of nicotine is facilitated due to the high pH value obtained.

A further advantage of the above embodiment may be that the need for preservative may be decreased or even eliminated and that low amounts of such preservatives may be used if not absent.

Also, the high pH value obtained may advantageously provide for a tingling sensation in the mouth which may be perceived as a desirable mouthfeel, e.g. due to resemblance with tobacco-based pouch products.

In an advantageous embodiment of the invention, the pH regulating agent is selected from the group consisting of Acetic acid, Adipic acid, Citric acid, Fumaric acid, Glucono-b-lactone, Gluconic acid, Lactic acid, Malic acid, Maleic acid, Tartaric acid, Succinic acid, Propionic acid, Ascorbic acid, Phosphoric acid, Sodium orthophosphate, Potassium orthophosphate, Calcium orthophosphate, Sodium diphosphate, Potassium diphosphate, Calcium diphosphate, Pentasodium triphosphate, Pentapotassium triphosphate, Sodium polyphosphate, Potassium polyphosphate, Carbonic acid, Sodium carbonate, Sodium bicarbonate, Potassium carbonate, Calcium carbonate, Magnesium carbonate, Magnesium oxide, or any combination thereof.

In an advantageous embodiment of the invention, the pH regulating agent is a basic pH regulating agent, such as a basic buffering agent and/or such as Sodium carbonate, Sodium bicarbonate, Potassium carbonate, Potassium bicarbonate, Magnesium carbonate, or any combination thereof.

In an embodiment, xylitol, maltitol, mannitol, erythritol, isomalt, sorbitol, lactitol, and mixtures thereof may be used as the at least one sugar alcohol. The at least one sugar alcohol may also comprise further sugar alcohols. As an example embodiment, hydrogenated starch hydrolysates may be used, which comprises a mixture of sorbitol, maltitol and further sugar alcohols.

In an advantageous embodiment of the invention, the at least one sugar alcohol is selected from xylitol, maltitol, mannitol, erythritol, isomalt, sorbitol, lactitol, and mixtures thereof.

In an advantageous embodiment of the invention, the at least one sugar alcohol is selected from xylitol, maltitol, mannitol, erythritol, isomalt, lactitol, and mixtures thereof.

In an embodiment of the invention, the at least one sugar alcohol comprises xylitol and/or erythritol.

In an advantageous embodiment of the invention, the pouch composition comprises at least two sugar alcohols.

It is noted that different sugar alcohols may be applied for the purpose of taste and salivation, where the sugar alcohol composition is made of different sugar alcohols having different properties with respect to storage, bacteria growth, processability and/or taste.

In an embodiment of the invention, the at least two sugar alcohols are selected from xylitol, maltitol, mannitol, erythritol, and isomalt.

In an advantageous embodiment of the invention, the pouch composition comprises sugar alcohol in an amount of at least 1% by weight of the composition, such as at least 2% by weight of the composition, such as at least 5% by weight of the composition, such as at least 10% by weight of the composition.

It is noted that a bulk density between 0.2 g/cm3 and 0.8 g/cm3, such as between 0.3 g/cm3 and 0.7 g/cm3, such as between 0.3 g/cm3 and 0.6 g/cm3, such as between 0.4 and 0.5 g/cm3 in relation to the composition including sugar alcohol in the amount of at least 1% by weight of the composition, such as at least 2% by weight of the composition, such as at least 5% by weight of the composition, such as at least 10% by weight of the composition does provide an attractive dissolving of the pouch content, including the nicotine, when put into contact with the mucosa.

In an advantageous embodiment of the invention, the pouch composition comprises sugar alcohol in an amount of 1 to 80% by weight of the composition, such as 2 to 70% by weight of the composition, such as 5 to 60% by weight of the composition, such as 10 to 50% by weight of the composition.

In an embodiment of the invention the pouch composition comprises sugar alcohol in an amount of 5 to 40% by weight of the composition, such as 5-30% by weight of the composition.

In an advantageous embodiment of the invention, the sugar alcohol comprises a DC (direct compressible) grade sugar alcohol.

In an advantageous embodiment of the invention, at least 50% by weight of the sugar alcohol is a DC (direct compressible) grade sugar alcohol.

In an embodiment of the invention the sugar alcohol comprises a non-DC (non-direct compressible) grade sugar alcohol.

In an advantageous embodiment of the invention, the water-insoluble fiber is a plant fiber.

In an advantageous embodiment of the invention, the water-insoluble fiber is selected from wheat fibers, pea fibers, rice fiber, maize fibers, oat fibers, tomato fibers, barley fibers, rye fibers, sugar beet fibers, buckwheat fibers, potato fibers, cellulose fibers, apple fibers, cocoa fibers, cellulose fibers, bran fibers, bamboo fibers, powdered cellulose, and combinations thereof.

Powdered cellulose within the scope of the invention is understood to be cellulose prepared by processing alpha-cellulose obtained as a pulp from strains of fibrous plant materials, such as wood pulp.

In an embodiment of the invention, the water-soluble fiber comprises or consists of cereal fibers.

In an embodiment of the invention, the water-soluble fiber comprises or consists of fruit and/or vegetable fibers.

In an advantageous embodiment of the invention, the water-insoluble composition comprises or consists of water-insoluble fiber selected from wheat fibers, oat fibers, pea fibers, powdered cellulose, or combinations thereof.

In an advantageous embodiment of the invention, the water-insoluble composition comprises or consists of water-insoluble fiber selected from wheat fibers, oat fibers, pea fibers, or combinations thereof.

In an advantageous embodiment of the invention, the water-insoluble composition comprises or consists of water-insoluble fiber selected from wheat fibers, oat fibers, or combinations thereof.

Non-limiting examples of usable water-insoluble fibers include VITACEL WF 600, VITACEL HF 600, VITACEL P95, VITACEL WF 200, VITACEL L00, VITACEL Erbsenfaser EF 150, VITACEL bamboo fiberbaf 90, VITACEL HF 600, VITACEL Cellulose L700G, VITACEL PF200, VITACEL potatofiber KF200, VITACEL bamboo fiberhaf BAF40, VITACEL Haferfaser/oatfiber HF-401-30 US.

Non-limiting examples of usable powdered cellulose include VITACEL L 00, VITACEL Cellulose L700G, VITACEL LC1000, VITACEL L600-20, VITACEL L600 etc.

In an embodiment, the powdered cellulose is chemically unmodified. Thus, powdered cellulose may be chemically unmodified cellulose fibers, which do not include e.g. microcrystalline cellulose (MCC).

In an advantageous embodiment of the invention, the water-insoluble fiber has a water binding capacity of at least 200%, such as at least 300%, such as at least 400%.

An advantage of the above embodiment may be that the high water-binding capacity enables pouch compositions having a high water-content.

Furthermore, the pouches having a high water-content where found to have a desirable texture and mouthfeel may while still being able to store manufactured pouches together in abutment e.g. in cans etc. without sticking too much together to result in ruptures of the pouches when being removed.

In an embodiment of the invention, the water-insoluble fiber has a water binding capacity of 300 to 1500%, such as 400 to 1300%.

In an embodiment of the invention, the water-insoluble fiber has a water binding capacity of 200% to 1500%, such as 300 to 1300%, such as 200 to 800%, such as 300 to 800%, such as 400 to 600%.

In an embodiment of the invention, the water-insoluble fiber has a water binding capacity of 200 to 1500%, such as 300 to 1300%, such as 300 to 900%, such as 300 to 700%, such as 400 to 700%.

In an embodiment of the invention, the water-insoluble fiber has a water binding capacity of 200 to 1500%, such as 400 to 1500%, such as 500 to 1500%, such as 500 to 1200%, such as 500 to 1000%.

In an advantageous embodiment of the invention, the water-insoluble fiber has a swelling capacity of at least 5.0 mL/g, such as 5.0-20 mug.

An advantage of the above embodiment is that the amount of water-insoluble fiber can be reduced without compromising the mouthfeel during use. If an amount of water-insoluble fiber is substituted for a water-soluble component, the swelling of the water-insoluble fiber will during use counteract the dissolution of the water-soluble component, thereby the user will not experience any decrease in pouch content during use.

In an advantageous embodiment of the invention, the water-insoluble composition comprises or consists of water-insoluble fiber in an amount between 5 and 50% by weight of the pouch composition and a water content of 15 to 70% by weight of said pouch composition.

In an advantageous embodiment of the invention, the water-insoluble fibers are selected from pea fibers, powdered cellulose, and combinations thereof, and wherein the pouch composition comprises flavor in an amount of no more than 10% by weight of the pouch composition.

In an embodiment of the invention, the pouch composition comprises water-insoluble fibers selected from pea fibers and powdered cellulose, or a combination thereof, and flavor in an amount of 0.01-10% by weight of the pouch composition.

In an advantageous embodiment of the invention, the water-insoluble fiber has a density of 50 to 500 gram per Liter, such as 100 to 400 gram per Liter, such as 200 to 300 gram per Liter.

In an advantageous embodiment of the invention, the pouch composition has an angle of repose of at least 40 degrees, such as at least 45 degrees, such as at least 50 degrees.

Thus, in the above embodiment the flowability is rather low.

In an embodiment, the angle of repose may be 45 to 70 degrees, such as 45 to 70 degrees, such as 50 to 70 degrees.

The angle of repose may be measured by slowly pouring 50 g of pouch composition from a height of about 10 cm onto a flat, horizontal surface.

In an advantageous embodiment of the invention, the pouch composition comprises water in an amount of 8-60% by weight of the composition, such as 8-50% by weight of the composition, such as 8-40% by weight of the composition, such as 20-40% by weight of the composition.

In an embodiment of the invention, the pouch composition comprises water in an amount of 8-60% by weight of the composition, such as 10-60% by weight of the composition, such as 15-60% by weight of the composition, such as 20-60% by weight of the composition.

In an embodiment of the invention, the pouch composition comprises water in an amount of 8-60% by weight of the composition, such as 8-50% by weight of the composition, such as 8-40% by weight of the composition, such as 8-30% by weight of the composition.

In an advantageous embodiment of the invention, the pouch composition comprises water in an amount of 10-40% by weight of the composition.

In an advantageous embodiment of the invention, the pouch composition comprises water in an amount of 20-65% by weight of the composition, such as 20-60% by weight of the composition, such as 20-50% by weight of the composition, such as 20-40% by weight of the composition.

In an advantageous embodiment of the invention, the pouch composition has a water content of 15 to 65% by weight of said pouch composition, such as 15 to 50% by weight of said pouch composition, such as 15 to 40% by weight of said pouch composition, such as 15 to 30% by weight of said pouch composition, such as 15 to 25% by weight of said pouch composition.

The water may be added as a separate component of be fully or partly mixed into other components, such as fibers. E.g. when adding free-base nicotine as a mixture of free-base nicotine with ion exchange resin and water, a significant amount of water of the final pouch composition may come from the free-base nicotine-ion exchange resin-water pre-mixture. For example, if the final amount pouch composition comprises 5% water from free-base nicotine-ion exchange resin-water pre-mixture, then up to one third of the water in the pouch composition derives from the free-base nicotine-ion exchange resin-water pre-mixture.

In an advantageous embodiment of the invention, the pouch composition comprises water and water-insoluble fiber in a weight ratio of no more than 3.0, such as no more than 2.5, such as no more than 2.0, such as no more than 1.5, such as no more than 1.0.

In an embodiment, the pouch composition comprises water and water-insoluble fiber in a weight ratio of 3.0 to 0.2, such as 2 to 0.2, such as 2.0 to 1.0, such as 1.5 to 0.5.

Thus, the weight ratio above has in the numerator the content of water in percentage by weight of the pouch composition, and in the denominator the content water-insoluble fiber in percentage by weight of the pouch composition.

Having a water content within the scope of this invention may facilitate a fast release within the initial fast release period, such as within the first 120 seconds, since the pouch is already wetted or partly wetted with water from start of use.

On the other hand, the water content should not be too high. Having a too high water content could influence the liquid diffusion both into the pouch as well as out of the pouch. A fully wetted pouch may have a lower liquid diffusion both into and out of the pouch when used, whereas as partly wetted pouch may have higher liquid diffusion both into and out of the pouch. A pouch with a low liquid diffusion may thus have a lower release of nicotine, e.g. after 10 minutes.

In an embodiment of the invention, the pouch composition has a water content of no more than 60% by weight of said pouch composition, such as no more than 50% by weight of said pouch composition, such as no more than 40% by weight of said pouch composition, such as no more than 30% by weight of said pouch composition.

In an advantageous embodiment of the invention, the pouch composition is free of tobacco, tobacco fibers and fibers derived from tobacco.

In some alternative embodiments, the pouch composition may comprise minor amounts of tobacco. Any, nicotine provided as part of tobacco, such as e.g. powdered tobacco, is further to the free-base nicotine. Such tobacco may e.g. be included to provide tobacco flavor.

In an embodiment, the pouch composition may comprise tobacco, tobacco fibers, or fibers derived from tobacco in an amount of 0.1 to 5.0% by weight of the pouch composition, such as in an amount of 0.1 to 3.0% by weight of the pouch composition. Thus, while the pouch composition in some embodiments may comprise small amounts of tobacco, this is in addition to the free-base nicotine, and thus the pouch composition is not tobacco based.

In an embodiment of the invention, the pouch composition comprises less than 5.0% by weight of tobacco, such as less than 3.0% by weight of the pouch composition, such as less than 1.0% by weight of the pouch composition, such as less than 0.5% by weight of the pouch composition, such as less than 0.1% by weight of the pouch composition, such as being free of tobacco.

In an embodiment of the invention, the water-insoluble composition does not comprise tobacco, tobacco fibers or fibers derived from tobacco. Thus, in this embodiment, the water-insoluble fibers are non-tobacco fibers, i.e. does not comprise tobacco, tobacco fibers, or fibers derived from tobacco.

In an embodiment of the invention, the pouch composition is free of microcrystalline cellulose (MCC), such as free of cellulose.

In an embodiment of the invention, the pouch composition comprises cellulose and is free of microcrystalline cellulose (MCC).

In an advantageous embodiment of the invention, the pouch composition said composition comprises sugar alcohol selected from the group consisting of sorbitol, erythritol, xylitol, lactitol, maltitol, mannitol, hydrogenated starch hydrolyzates, isomalt, or any combination thereof and wherein the composition comprises said sugar alcohol in an amount of 1-80% by weight of the pouch composition, such as 5-70% by weight of the pouch composition, such as 10-60% by weight of the pouch composition.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof,
wherein the composition comprises said sugar alcohol in an amount of 1-80% by weight of the pouch composition, such as 5-70% by weight of the pouch composition, such as 10-60% by weight of the pouch composition,
and wherein said composition further comprises water-insoluble fibers in an amount of between 5 and 50% by weight of the pouch composition, such as between 10 and 30% by weight of the pouch composition.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof,
wherein the composition comprises said sugar alcohol in an amount of 1-80% by weight of the pouch composition, such as 5-70% by weight of the pouch composition, such as 10-60% by weight of the pouch composition,
wherein said composition further comprises water-insoluble fibers in an amount of between 5 and 50% by weight of the pouch composition, such as between 10 and 30% by weight of the pouch composition,
and therein the water-insoluble composition comprises or consists of water-insoluble fiber, such as wheat fibers, oat fibers, pea fibers, powdered cellulose, or combinations thereof.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof,
wherein the composition comprises said sugar alcohol in an amount of 1-80% by weight of the pouch composition, such as 5-70% by weight of the pouch composition, such as 10-60% by weight of the pouch composition,
wherein said composition further comprises water-insoluble fibers in an amount of between 5 and 50% by weight of the pouch composition, such as between 10 and 30% by weight of the pouch composition,
and wherein the water-insoluble composition comprises or consists of water-insoluble fiber, such as wheat fibers, oat fibers, pea fibers, powdered cellulose, or combinations thereof and wherein the pouch composition comprises flavor in an amount between 0.01 and 15% by weight of the pouch composition, such as between 0.1 and 15% by weight of the pouch composition, such as between 1 and 10% by weight of the pouch composition, such as between 3 and 10% by weight of the pouch composition.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof,
wherein the composition comprises said sugar alcohol in an amount of 1-80% by weight of the pouch composition, such as 5-70% by weight of the pouch composition, such as 10-60% by weight of the pouch composition,
wherein said composition further comprises water-insoluble fibers in an amount of between 5 and 50% by weight of the pouch composition, such as between 10 and 30% by weight of the pouch composition,
wherein the water-insoluble composition comprises or consists of water-insoluble fiber, such as wheat fibers, oat fibers, pea fibers, powdered cellulose, or combinations thereof and wherein the pouch composition comprises flavor in an amount between 0.01 and 15% by weight of the pouch composition, such as between 0.1 and 15% by weight of the pouch composition, such as between 1 and 10% by weight of the pouch composition, such as between 3 and 10% by weight of the pouch composition and wherein the flavor is oil-based.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof,
wherein the composition comprises said sugar alcohol in an amount of 1-80% by weight of the pouch composition, such as 5-70% by weight of the pouch composition, such as 10-60% by weight of the pouch composition,
wherein said composition further comprises water-insoluble fibers in an amount of between 5 and 50% by weight of the pouch composition, such as between 10 and 30% by weight of the pouch composition, and wherein the pouch composition comprises a pH regulating agent selected from the group consisting of Acetic acid, Adipic acid, Citric acid, Fumaric acid, Glucono-δ-lactone, Gluconic acid, Lactic acid, Malic acid, Maleic acid, Tartaric acid, Succinic acid, Propionic acid, Ascorbic acid, Phosphoric acid, Sodium orthophosphate, Potassium orthophosphate, Calcium orthophosphate, Sodium diphosphate, Potassium diphosphate, Calcium diphosphate, Pentasodium triphosphate, Pentapotassium triphosphate, Sodium polyphosphate, Potassium polyphosphate, Carbonic acid, Sodium carbonate, Sodium bicarbonate, Potassium carbonate, Calcium carbonate, Magnesium carbonate, Magnesium oxide, or any combination thereof.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof, wherein the composition comprises said sugar alcohol in an amount of 1-80% by weight of the pouch composition, such as 5-70% by weight of the pouch composition, such as 10-60% by weight of the pouch composition, wherein said composition further comprises water-insoluble fibers in an amount of between 5 and 50% by weight of the pouch composition, such as between 10 and 30% by weight of the pouch composition, and wherein the pouch composition comprises a pH regulating agent which is a basic pH regulating agent, such as a basic buffering agent and/or such as Sodium carbonate, Sodium bicarbonate, Potassium carbonate, Potassium bicarbonate, Magnesium carbonate, or any combination thereof.

In an advantageous embodiment of the invention, the pouch composition further comprises a humectant.

In an embodiment, the humectant is selected from the list of glycerol, propylene glycol, alginate, pectin, modified starch, hydroxypropyl cellulose, triacetin, polyethylene glycol (PEG), xanthan gum, and combinations thereof.

In an embodiment, the humectant is or comprises humectant in an amount of 0.5 to 10%, such as 0.5 to 5% by weight of the pouch composition, such as 1-3% by weight of the pouch composition.

The humectant may attract and retain water in the oral cavity during use. However, the humectant may additionally moderate the release of nicotine, e.g. to facilitate a sustained release of nicotine.

In an embodiment, the humectant is or comprises alginate, such as sodium alginate, e.g. in an amount of 0.5 to 10%, such as 0.5 to 5% by weight of the pouch composition, such as 1-3% by weight of the pouch composition.

In an embodiment of the invention, the pouch composition further comprises glycerol.

In an embodiment of the invention, the pouch composition further comprises modified starch.

In an embodiment of the invention, the pouch composition further comprises hydroxypropyl cellulose (HPC).

In an advantageous embodiment of the invention, the pouch composition comprises a glidant, such as silicon dioxide, e.g. in an amount of between 0.5 and 5% by weight of the composition, such as 1-3% by weight of the composition.

In an embodiment of the invention, the glidant is selected from talc powder, colloidal silica, silicon dioxide, starch, magnesium stearate, and combinations thereof.

In an advantageous embodiment of the invention, the pouch composition comprises flavor, e.g. in an amount of 0.01 and 20% by weight of the pouch composition, such as in an amount of 0.01 to 15% by weight of the pouch composition.

In an embodiment of the invention, the pouch composition comprises flavor in an amount between 0.01 and 15% by weight of the pouch composition, such as between 0.1 and 15% by weight of the pouch composition, such as between 1 and 10% by weight of the pouch composition, such as between 3 and 10% by weight of the pouch composition.

The properties of the water-insoluble component may influence the release of the flavor from the pouch composition and thereby possible influence the perception of flavor by the user.

In an embodiment of the invention the water-insoluble fiber may cause a higher or lower perception of flavor to the user.

In an embodiment of the invention, the pouch composition comprises flavor in an amount of no more than 10% by weight of the pouch composition, such as no more than 8% by weight of the pouch composition, such as no more than 5% by weight of the pouch composition.

In an embodiment of the invention, the pouch composition comprises flavor in an amount of 0.01-10% by weight of the pouch composition, such as 0.01-8% by weight of the pouch composition, such as 0.01-5% by weight of the pouch composition.

In an embodiment of the invention, the pouch composition is substantially homogenous.

For example, when mixing at least 90% by weight of the total amount of dry ingredients before adding nicotine followed by water, such as before adding nicotine followed by water and liquid flavors, if any, a more homogeneous pouch composition may be obtained, having an even distribution of nicotine.

In an advantageous embodiment of the invention, the content of nicotine between a series of at least 10 oral pouches comprising said pouch composition holds a relative standard deviation (RSD) below 10%, preferably below 8%, more preferably at most 6%, even more preferably at most 4%, most preferably at most 2%.

In an embodiment of the invention, the content of the nicotine between a series of at least 10 oral pouches comprising said pouch composition holds a relative standard deviation (RSD) of 0.1-10%, preferably 0.1-8%, more preferably 0.1-6%, even more preferably 0.1-4%, and most preferably 0.1-2%.

Homogeneity of a pouch composition may be assessed by evaluating the distribution between individual pouches of single components of the composition.

For example, the standard deviation of the nicotine content, i.e. nicotine content uniformity (CU), relates to the homogeneity of the pouch composition. Pouches prepared from the same pouch composition and having a low standard deviation on the nicotine content will have a high pouch composition homogeneity, whereas pouches prepared from the same pouch composition and having a high standard deviation on the nicotine content will have a low pouch composition homogeneity.

In an advantageous embodiment of the invention, said composition comprises sugar alcohol selected from the group consisting of sorbitol, erythritol, xylitol, lactitol, maltitol, mannitol, hydrogenated starch hydrolyzates, isomalt, or any combination thereof and wherein the composition comprises said sugar alcohol in an amount of 1-80% by weight of the pouch composition, such as 5-70% by weight of the pouch composition, such as 10-60% by weight of the pouch composition.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof,
- wherein the composition comprises said sugar alcohol in an amount of 1-80% by weight of the pouch composition, such as 5-70% by weight of the pouch composition, such as 10-60% by weight of the pouch composition,
- and wherein said composition further comprises water-insoluble fibers in an amount of between 5 and 50% by weight of the pouch composition, such as between 10 and 30% by weight of the pouch composition.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof,
- wherein the composition comprises said sugar alcohol in an amount of 1-80% by weight of the pouch composition, such as 5-70% by weight of the pouch composition, such as 10-60% by weight of the pouch composition,
- wherein said composition further comprises water-insoluble fibers in an amount of between 5 and 50% by weight of the pouch composition, such as between 10 and 30% by weight of the pouch composition, and therein the water-insoluble composition comprises or consists of water-insoluble fiber, such as wheat fibers, oat fibers, pea fibers, powdered cellulose, or combinations thereof.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof,
- wherein the composition comprises said sugar alcohol in an amount of 1-80% by weight of the pouch composition, such as 5-70% by weight of the pouch composition, such as 10-60% by weight of the pouch composition,
- wherein said composition further comprises water-insoluble fibers in an amount of between 5 and 50% by weight of the pouch composition, such as between 10 and 30% by weight of the pouch composition,
- and wherein the water-insoluble composition comprises or consists of water-insoluble fiber, such as wheat fibers, oat fibers, pea fibers, powdered cellulose, or combinations thereof and wherein the pouch composition comprises flavor in an amount between 0.01 and 15% by weight of the pouch composition, such as between 0.1 and 15% by weight of the pouch composition, such as between 1 and 10% by weight of the pouch composition, such as between 3 and 10% by weight of the pouch composition.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof,
- wherein the composition comprises said sugar alcohol in an amount of 1-80% by weight of the pouch composition, such as 5-70% by weight of the pouch composition, such as 10-60% by weight of the pouch composition,
- wherein said composition further comprises water-insoluble fibers in an amount of between 5 and 50% by weight of the pouch composition, such as between 10 and 30% by weight of the pouch composition,
- wherein the water-insoluble composition comprises or consists of water-insoluble fiber, such as wheat fibers, oat fibers, pea fibers, powdered cellulose, or combinations thereof and wherein the pouch composition comprises flavor in an amount between 0.01 and 15% by weight of the pouch composition, such as between 0.1 and 15% by weight of the pouch composition, such as between 1 and 10% by weight of the pouch composition, such as between 3 and 10% by weight of the pouch composition and wherein the flavor is oil-based.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof,
- wherein the composition comprises said sugar alcohol in an amount of 1-80% by weight of the pouch composition, such as 5-70% by weight of the pouch composition, such as 10-60% by weight of the pouch composition,
- wherein said composition further comprises water-insoluble fibers in an amount of between 5 and 50% by weight of the pouch composition, such as between 10 and 30% by weight of the pouch composition,
- and wherein the pouch composition comprises a pH regulating agent selected from the group consisting of Acetic acid, Adipic acid, Citric acid, Fumaric acid, Glucono-6-lactone, Gluconic acid, Lactic acid, Malic acid, Maleic acid, Tartaric acid, Succinic acid, Propionic acid, Ascorbic acid, Phosphoric acid, Sodium orthophosphate, Potassium orthophosphate, Calcium orthophosphate, Sodium diphosphate, Potassium diphosphate, Calcium diphosphate, Pentasodium triphosphate, Pentapotassium triphosphate, Sodium polyphosphate, Potassium polyphosphate, Carbonic acid, Sodium carbonate, Sodium bicarbonate, Potassium carbonate, Calcium carbonate, Magnesium carbonate, Magnesium oxide, or any combination thereof.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof,
- wherein the composition comprises said sugar alcohol in an amount of 1-80% by weight of the pouch composition, such as 5-70% by weight of the pouch composition, such as 10-60% by weight of the pouch composition,
- wherein said composition further comprises water-insoluble fibers in an amount of between 5 and 50% by weight of the pouch composition, such as between 10 and 30% by weight of the pouch composition,
- and wherein the pouch composition comprises a pH regulating agent which is a basic pH regulating agent, such as a basic buffering agent and/or such as Sodium carbonate, Sodium bicarbonate, Potassium carbonate, Potassium bicarbonate, Magnesium carbonate, or any combination thereof.

The invention further relates to an oral pouched nicotine product comprising
- a saliva-permeable pouch and a nicotine pouch composition,
- the nicotine pouch composition comprising
- at least one sugar alcohol,
- at least one water-insoluble fiber,
- water in an amount of 8-65% by weight of the composition, and
- nicotine,
- wherein the pouch has a maximum inner pouch volume and wherein the nicotine pouch composition has a volume corresponding to at least 65% of said maximum inner pouch volume.

An advantage of the invention may be that a very desirable mouthfeel is obtained. Previously focus has been pronounced on the pouch composition, which of course plays an important role. The present inventors have surprisingly found that by filling the pouch to close to its maximum inner volume, the mouthfeel is markedly improved.

Furthermore, by using the claimed pouch composition, a high mobility of the composition may be obtained, which provides for effectively filling of the pouch without resulting in excessive compression of the pouch composition. Thereby, a relatively low density, high volume pouch may be obtained. The low density facilitates effective contacting with saliva during use, which again facilitates fast release of e.g. nicotine. At the same time, a low density advantageously lowers the need for raw materials and thereby decreases production costs.

A further advantage of the present invention may be that a high mobility of the pouch composition is obtained. This high mobility may be used to obtain a high degree of filling of the pouch, preferably with a relatively low density of pouch composition. Inclusion of significant amounts of water in compositions comprising sugar alcohol and fiber was expected to result in significant problems with manufacturing of pouched products. A typical measure of processability of powdered composition is flowability, where a certain minimum flowability would be required to effectively handle the compositions. The high water content would typically result in a very low flowability, indicating a very poor processability.

Nevertheless, the obtained pouch compositions showed to indeed be processable, demonstrating that these had a mobility within a processable range. This high mobility allowed pouches to be filled with a high degree of filling and maintaining a relatively low density composition. This advantageously allows the produced pouches to have a high volume while keeping the consumption of raw materials low. This is surprising, as it was expected that adding water would result in a poor mobility and a high density composition, which would result in complicated manufacturing and high raw materials costs unless the user experience associated with a full pouch was compromised.

In an advantageous embodiment of the invention, the composition has a bulk density less than 0.8 g/cm3, such as less than 0.7 g/cm3, such as less than 0.6 g/cm3, such as less than 0.5 g/cm3 in the pouch.

In an advantageous embodiment of the invention, the pouch comprises a water-permeable membrane, comprising e.g. woven or non-woven fabric.

Typically, the pouch membrane comprise openings, where the characteristic opening dimension is adapted to a characteristic dimension of the pouch composition so as to retain the pouch composition inside the pouch before use and/or to retain a part of the pouch composition, such as an water-insoluble composition, inside the pouch during use.

In order to obtain a pouch membrane having suitable opening dimensions in view of the pouch composition to be used, the material for the pouch membrane may be selected accordingly, e.g. comprising e.g. woven and/or non-woven fabric.

In other words, according to the various embodiments, the pouch membrane allows passage of saliva and prevents or inhibits passage of undissolved composition and the water-insoluble fibers. The pouch membrane may be of any suitable material e.g. woven or non-woven fabric (e.g. cotton, fleece etc.), heat sealable non-woven cellulose, such as long fiber paper, or other polymeric materials such as a synthetic, semi-synthetic or natural polymeric material. An example of suitable material for the pouch membrane is paper made of pulp and a small amount of wet strength agent. A material suitable for use must provide a semi-permeable membrane layer to prevent the powder or composition from leaving the bag or pouch during use. Suitable materials are also those that do not have a significant impact on the release of nicotine from the pouch.

In more detail, regarding the material, the pouch membrane may be a natural, synthetic, semi-synthetic hydrophilic or hydrophobic membrane. It may be made from one or more biocompatible and physiologically acceptable polymeric material. Examples of suitable materials for the pouch membrane are cellulose acetate and derivatives thereof, carboxymethyl cellulose, polycellulose ester, other cellulose derivatives including ethylcellulose, propylcellulose, polyethylene, polypropylene, polystyrene, polyvinyl chloride, polyvinyl acetate, polymers of methacrylates and acrylates, natural rubber, polycarbonate, polyethylene terephthalate, polyester, polyamide and nylon. Other suitable materials are mentioned herein before.

Rayon fibers (i.e. regenerated cellulose), such as viscose rayon fibers may also be used, e.g. in combination with an acrylic polymer that acts as binder in the nonwoven material and provides for heat-sealing of the pouch membrane during manufacturing thereof. Other binders, such as one or more copolymers of vinyl acetate and acrylic acid ester, may also be used.

Suitable pouch membranes for are available under the trade names TABOKA, CATCH dry, ETTAN, GENERAL . GRANIT, GOTEBORGS RAPE, GROVE Snus White, METROPOL Kaktus, MOCCA Anis, MOCCA Mint, MOCCA Wintergreen, KICKS, PROBE, PRINCE, SKRUF, TRE ANKRARE, CAMEL Snus Original, CAMEL Snus Frost and CAMEL Snus Spice. The pouch membrane provides a liquid-permeable container of a type that may be considered to be similar in character to the mesh-like type of material that is used for the construction of a tea bag. Desired components of the nicotine composition to be released diffuse through the pouch membrane and into the mouth of the user.

Materials of the pouch membrane may have the form of a mesh, screen, perforated paper, permeable fabric, or the like. For example, pouch material manufactured from a mesh-like form of rice paper, or perforated rice paper, may dissolve in the mouth of the user. In some exemplary embodiments, the materials of the pouch membrane may be manufactured using water dispersible film forming materials (e.g., binding agents such as alginates, carboxymethylcellulose, xanthan gum, pullulan, and the like), as well as those materials in combination with materials such as ground cellulosics (e.g., fine particle size wood pulp). Preferred pouch materials, though water dispersible or dissolvable, may be designed and manufactured such that under conditions of normal use, a significant amount of the nicotine contents permeates through the pouch material prior to the time that the pouch undergoes loss of its physical integrity. If desired, flavoring ingredients, disintegration aids, and other desired components, may be incorporated within, or applied to, the pouch material.

Examples of various types of pouch membrane materials set forth in U.S. Pat. No. 5,167,244 to Kjerstad. Fleece materials for use as pouch membranes are described e.g. in WO 2008/152469, GB 673,587, and EP 2 692 254.

In an embodiment of the invention the membrane comprises water insoluble fibers of different origin than the water insoluble fibers contained in the pouched product.

In an embodiment of the invention both the water insoluble fibers of the membrane and the water-insoluble fibers of the pouch composition comprises natural fibers.

In an embodiment of the invention both the water insoluble fibers of the membrane and the water-insoluble fibers of the pouch composition are natural fibers.

In an advantageous embodiment of the invention, the pouched product comprises said pouch in an amount of up to 20 percent by weight of said pouched product, such as in an amount of up to 15 percent by weight of said pouched product.

In an advantageous embodiment of the invention, the pouched product comprises said pouch in an amount of 3-20 percent by weight of said pouched product, such as in an amount of 5-15 percent by weight of said pouched product.

In an advantageous embodiment of the invention, the pouch has a maximum inner pouch volume and wherein the nicotine pouch composition has a volume corresponding to at least 70% of said maximum inner pouch volume, such as at least 80% by said maximum inner pouch volume, such as at least 90% by said maximum inner pouch volume, such as at least 95% by said maximum inner pouch volume.

In an embodiment of the invention, the pouch has a maximum inner pouch volume and wherein the nicotine pouch composition has a volume corresponding to at least 90% of said maximum inner pouch volume, such as at least 95% by said maximum inner pouch volume.

In an advantageous embodiment of the invention, the maximum inner pouch volume is at least 0.5 mL, such as at least 1.0 mL.

In an embodiment, the maximum inner pouch volume is between 0.5 mL and 3.0 mL, such as between 1.0 and 2.0 mL.

In an advantageous embodiment of the invention, the oral nicotine pouched product according to the invention or any of its embodiments comprises the nicotine pouch composition according to the invention or any of its embodiments.

The invention further relates to a method of manufacturing an oral pouched product according to the invention or any of its embodiments, the method comprising the steps of adding the providing the pouch composition according to the invention or any of its embodiments,
providing the saliva-permeable pouch,
adding the pouch composition to said pouch, and
sealing the pouch.

DETAILED DESCRIPTION OF THE INVENTION

As used herein the term "nicotine" refers to nicotine used as a refined/isolated substance. Particularly, nicotine does not refer to tobacco materials having a content of nicotine.

As used herein the term "nicotine pouch composition" refers to the composition for use in a pouched product, i.e. in pouches for oral use comprising nicotine. Also, the terms "nicotine pouch composition" and "pouch composition" is used interchangeably. The nicotine pouch composition is not a tobacco-based pouch composition. In some embodiments, the nicotine pouch composition may comprise small amounts of tobacco as a flavoring, below 2% by weight of the composition. In other embodiments, the nicotine pouch composition is free of tobacco.

As used herein the term "free-base nicotine" refers to non-protonated form of nicotine, and therefore does not include nicotine salts and nicotine provided as a complex between nicotine and an ion exchange resin.

Nevertheless, the free-base nicotine may be mixed with an amount of ion exchange resin or water-soluble compositions such as sugar alcohols or water-soluble fibers. While free-base nicotine includes both free-base nicotine extracted from tobacco as well as synthetically manufactured free-base nicotine, the free-base nicotine is not provided in the form of tobacco or powdered tobacco. Typically, free-base nicotine is provided as a liquid.

As used herein the term "pouch" is intended to mean a container typically formed by a web of a fibrous material enclosing a cavity. The pouch is designed for administration of an active ingredient in the oral cavity, and thus it is adapted for oral use, it is non-toxic and not water-soluble. The fibrous material may e.g. form a woven or non-woven web or fabric. The pouch may for example be sealed by bonding two corresponding pieces of web or fabric to each other along their edges to form a cavity for the nicotine and the non-water-soluble composition. In order to release the nicotine, flavor and other water-soluble substances, the pouch is water-permeable so as to allow saliva from the oral cavity to penetrate the pouch and enter the cavity, where the saliva can come into contact with the nicotine, flavor and other water-soluble substances, whereby the nicotine, flavor and other water-soluble substances are released from the oral pouch.

As used herein the term "powder composition" refers to composition in the form of powder, i.e. as a particulate material having a relatively small particle size, for example between 1 and 1200 micrometer. Particularly, by powder composition is not meant a powdered tobacco.

As used herein the term mobility is a parameter for powder processability when flowability is not applicable.

As used herein the term "humectant" is understood as a moistening agent used to attract moisture or water in the form of saliva. Humectants may typically include suitably hygroscopic compositions. In some cases, humectants may also be described as moistening agents, due to their role in attraction of moisture. Examples of humectants include glycerol, propylene glycol, triacetin, modified starch, hydroxypropyl cellulose, alginate, pectin, xanthan gum, etc.

As used herein the term "water-soluble" refers to a relatively high water-solubility, for example a water-solubility of more than 5 gram of water-soluble composition or substance per 100 mL of water measured at 25 degrees Celsius and pH of 7.0. When referring to a "soluble" composition or substance, water-soluble is meant, unless otherwise stated.

As used herein the term "water-insoluble" refers to relatively low water-solubility, for example a water-solubility of less than 0.1 gram of water-soluble composition or substance per 100 mL of water measured at 25 degrees Celsius and pH of 7.0. When referring to "insoluble", water-insoluble is meant unless otherwise stated.

As used herein the term "flavor" is understood as having its ordinary meaning within the art. Flavor includes liquid and powdered flavors. Thus, flavors do of course not include sweeteners (such as sugar, sugar alcohols and high intensity sweeteners), or acids providing pure acidity/sourness, nor compounds providing pure saltiness (e.g. NaCl) or pure bitterness. Flavor enhancers include substances that only provide saltiness, bitterness or sourness. Flavor enhancers thus include e.g. NaCl, Citric acid, ammonium chloride etc.

The pouches of the invention provide a nicotine release into the oral cavity. A release profile of nicotine may be obtained which both comprises a fast release period and a sustained release period.

As used herein the term "fast release" or "fast release period" may refer to the initial 2 minutes of the nicotine release profile, whereas the term "sustained release period refers" to the subsequent period of the release profile until end of experiment or end of use.

As used herein "release rate" describes the average release of nicotine per minute within a given period, for example if a pouch in the period from 2 minutes to 10 minutes further releases 16% of the nicotine dose, the release rate is 2% per minute within this given period. Alternatively, if a pouch in the period from 2 minutes to 10 minutes further releases 2 mg of nicotine, the release rate is 0.25 mg per minute within this given period. The release rate is determined only from the release data at the outer time points of the time period.

Typically, the pouches comprise openings, where the characteristic opening dimension is adapted to a characteristic dimension of the pouch composition so as to retain the pouch composition inside the pouch before use and/or to retain a part of the pouch composition, such as an water-insoluble composition, inside the pouch during use.

In order to obtain a pouch having suitable opening dimensions in view of the pouch composition to be used, the material for the pouch may be selected accordingly, e.g. comprising e.g. woven and/or non-woven fabric.

In other words, according to the various embodiments, the pouch forms a membrane allowing passage of saliva and prevents or inhibits passage of undissolved composition and the water-insoluble fibers. The membrane of the pouch may be of any suitable material e.g. woven or non-woven fabric (e.g. cotton, fleece etc.), heat sealable non-woven cellulose or other polymeric materials such as a synthetic, semi-synthetic or natural polymeric material. An example of suitable pouch material is paper made of pulp and a small amount of wet strength agent. A material suitable for use must provide a semi-permeable membrane layer to prevent the powder or composition from leaving the bag or pouch during use. Suitable materials are also those that do not have a significant impact on the release of nicotine from the pouch.

The pouch composition is filled into pouches and is maintained in the pouch by a sealing. An ideal pouch is chemically and physically stable, it is pharmaceutically acceptable, it is insoluble in water, it can be filled with powder and sealed, and it provides a semi-permeable membrane layer which prevent the powder from leaving the bag, but permit saliva and therein dissolved or sufficiently small suspended components from the pouch composition in the pouch, such as nicotine and flavor, to pass through said pouch.

The pouch may be placed in the oral cavity by the user. Saliva then enters into the pouch, and the nicotine and other components, which are soluble in saliva, start to dissolve and are transported with the saliva out of the pouch into the oral cavity, where the nicotine may be absorbed.

According to an embodiment of the invention, the pouch composition comprises one or more pH-regulating agent, such as a buffering agent.

In an embodiment of the invention, said pH-regulating agents are selected from the group consisting of Acetic acid, Adipic acid, Citric acid, Fumaric acid, Glucono-b-lactone, Gluconic acid, Lactic acid, Malic acid, Maleic acid, Tartaric acid, Succinic acid, Propionic acid, Ascorbic acid, Phosphoric acid, Sodium orthophosphate, Potassium orthophosphate, Calcium orthophosphate, Sodium diphosphate, Potassium diphosphate, Calcium diphosphate, Pentasodium triphosphate, Pentapotassium triphosphate, Sodium polyphosphate, Potassium polyphosphate, Carbonic acid, Sodium carbonate, Sodium bicarbonate, Potassium carbonate, Calcium carbonate, Magnesium carbonate, Magnesium oxide, or any combination thereof.

According to various embodiments of the invention, one or more sugar alcohols may be included in the pouch as part of the pouch composition, e.g. as a carrier or part thereof, as a humectant, or as a sweetener. Suitable sugar alcohols include sugar alcohols selected from the group of sorbitol, erythritol, xylitol, lactitol, maltitol, mannitol, hydrogenated starch hydrolyzates, isomalt, or any combination thereof.

In an embodiment of the invention the pouch composition comprises high intensity sweetener.

Preferred high intensity sweeteners include, but are not limited to sucralose, aspartame, salts of acesulfame, such as acesulfame potassium, alitame, saccharin and its salts, cyclamic acid and its salts, glycyrrhizin, dihydrochalcones, thaumatin, monellin, stevioside and the like, alone or in combination.

In an embodiment of the invention, the pouch composition comprises sugar and/or sugarless sweeteners, e.g. sugar alcohol.

In an embodiment of the invention, the pouch composition comprises sugar and/or sugarless sweeteners in the amount of 1.0 to about 80% by weight of the pouch composition, more typically constitute 5 to about 70% by weight of the pouch composition, and more commonly 10 to 30% by weight of the pouch composition or 5 to 25% by weight of the pouch composition. In some other embodiments, the sugar and/or sugarless sweeteners constitute 10 to 60% by weight of the pouch composition or 10-50% by weight of the pouch composition. Sugar and/or sugarless sweeteners may function both as a sweetener and also as a humectant. In some embodiments, inclusion of certain ingredients may limit the about amounts of sugar and/or sugarless sweeteners further. In some embodiments, the content of sugar and/or sugarless sweeteners in the pouch composition is no more than 20% by weight of the pouch composition, such as no more than 15% by weight of the pouch composition, such as no more than 10% by weight of the pouch composition, such as no more than 5% by weight of the pouch composition.

The sweeteners may often support the flavor profile of the pouch composition.

Sugar sweeteners generally include, but are not limited to saccharide-containing components commonly known in the art of pouches, such as sucrose, dextrose, maltose, saccharose, lactose, sorbose, dextrin, trehalose, D-tagatose, dried invert sugar, fructose, levulose, galactose, corn syrup solids, glucose syrup, hydrogenated glucose syrup, and the like, alone or in combination. These sugar sweeteners may also be included as a humectant.

The sweetener can be used in combination with sugarless sweeteners. Generally, sugarless sweeteners include components with sweetening characteristics but which are devoid of the commonly known sugars and comprise, but are not limited to, sugar alcohols, such as sorbitol, mannitol, xylitol, hydrogenated starch hydrolyzates, maltitol, isomalt, erythritol, lactitol and the like, alone or in combination. These sugarless sweeteners may also be included as a humectant.

In embodiments of the invention, the pouch composition further comprises water soluble fibers. Non-limiting examples of water-soluble fibers include inulin, polydextrose, and psyllium plant fibers. Other water-soluble dietary fibers may also be used.

In an embodiment of the invention the pouch composition comprises flavor. Flavor may typically be present in amounts between 0.01 and 15% by weight of the total composition of the pouch, such as between 0.01 and 5% by weight of the total composition. In an alternative embodiment the pouch composition may be free of flavor.

Non-exhaustive examples of flavors suitable in embodiments of the present invention are coconut, coffee, chocolate, vanilla, citrus such as grape fruit, orange, lime, bergamot, or lemon, menthol, liquorice, caramel aroma, honey aroma, peanut, walnut, cashew, hazelnut, almonds, pineapple, strawberry, raspberry, tropical fruits, cherries, cinnamon, peppermint, wintergreen, spearmint, eucalyptus, and mint, fruit essence such as from apple, pear, peach, strawberry, apricot, raspberry, cherry, pineapple, lemongrass, lime, chili (capsaicin), citrus, tobacco flavor, bergamot, and plum essence. The essential oils include peppermint, spearmint, menthol, eucalyptus, clove oil, bay oil, anise, thyme, cedar leaf oil, nutmeg, and oils of the fruits mentioned above.

In various embodiments of the invention, the pouch composition comprises a release controlling composition for controlling the release of the pouch composition and/or parts thereof, especially the nicotine.

The release controlling composition may, according to various embodiments, be selected from the group consisting of metallic stearates, modified calcium carbonate, hydrogenated vegetable oils, partially hydrogenated vegetable oils, polyethylene glycols, polyoxyethylene monostearates, animal fats, silicates, silicon dioxide, talc, magnesium stearates, calcium stearates, fumed silica, powdered hydrogenated cottonseed oils, hydrogenated vegetable oils, hydrogenated soya oil, emulsifiers, triglycerides, and mixtures thereof. Particularly, metallic stearates, such as magnesium stearate, may be advantageous.

The release controlling composition may be added to the pouch composition in various ways.

In an embodiment of the invention, the pouch composition is free of triglycerides.

For example, the release controlling composition may be added by full powder mixture during the last few minutes of the final mixing.

Alternatively, the release controlling composition may be added after granulation steps on a granulation premix.

Still further, the release controlling composition may be added only as a fraction of the pouch composition so two different release profiles of nicotine are achieved. Even further two or more fractions of the pouch composition may comprise different amounts of the release controlling composition, if any, thereby providing a more complex and tailored release profile of nicotine.

The release controlling composition, such as magnesium stearate, may have a sealing effect and can be used to control the release of the nicotine and the solubility of the pouch.

EXAMPLES

Example 1A—Preparation of Pouches Designed for Administration of Nicotine

The material of the pouches is heat sealable non-woven cellulose, such as long fiber paper. Pouches that are not in form of non-woven cellulose fabric may also be used according to the invention.

The powder is filled into pouches and is maintained in the pouch by a sealing.

Example 1B—Preparation of Pouches Designed for Administration of Nicotine

The material of the pouches is manufactured using rayon fibers, such as viscose rayon staple fibers. The pouch membrane is heat sealed along its edges except for an opening in one end into an inner cavity formed by the pouch membrane.

The powder is filled into pouches and is maintained in the pouch by a sealing.

Example 2A—Nicotine Premix I—Resin

A Stephan mixer (vacuum premixing) was charged with water, and nicotine was weighed and added, the mixer was closed and stirred for 5 minutes. Then ion exchange resin AMBERLITE® IRP64 was weighed and added to the mixer. The mixer was closed and stirred for 10-60 minutes.

Thereby, a mixture of nicotine and cation exchange resin was produced from the constituents stated in the below table 1.

TABLE 1

| Ingredients used to manufacture nicotine premix I. | | |
|---|---|---|
| Constituent | Amount (kg) | Amount (%) |
| Nicotine | 1.0 | 5.7 |
| Water | 12.5 | 71.4 |
| Resin | 4.0 | 22.9 |
| Total | 17.5 | 100.0 |

Nicotine:resin ratio: 1:4 (0.25)
% water in obtained nicotine-resin composition: 71.4

Example 2B—Nicotine Premix II—Resin

A 60 liter planetary BEAR VARIMIXER mixer was charged with water, and nicotine was weighed and added. The mixer was stirred at low speed for 1 minute at ambient temperature. Then ion exchange resin AMBERLITE® IRP64 was weighed and added to the mixer. The mixer was closed, stirred at high speed for 5 minutes, opened and scraped down, if necessary. Finally the mixer was stirred for further 5 minutes at high speed.

Thereby, a mixture of nicotine and cation exchange resin was produced from the constituents stated in the below table 2.

TABLE 2

| Ingredients used to manufacture nicotine premix II. | | |
|---|---|---|
| Constituent | Amount (kg) | Amount (%) |
| Nicotine | 1.08 | 13.2 |
| Water | 2.80 | 34.1 |
| Resin | 4.32 | 52.7 |
| Total | 8.20 | 100.0 |

Nicotine:resin ratio: 1:4 (0.25)
% water in obtained nicotine-resin composition: 34.1
The total process time was 20 minutes.

Example 2C—Nicotine Premix III—Resin

A 60 liter planetary BEAR VARIMIXER mixer was charged with water, and nicotine was weighed and added.

The mixer was stirred at low speed for 1 minute at ambient temperature. Then ion exchange resin AMBERLITE® IRP64 was weighed and added to the mixer. The mixer was closed, stirred at high speed for 5 minutes, opened and scraped down, if necessary. Finally, the mixer was stirred for further 5 minutes at high speed.

Thereby, a mixture of nicotine and cation exchange resin was produced from the constituents stated in the below table 3.

TABLE 3

Ingredients used to manufacture nicotine premix III.

| Constituent | Amount (kg) | Amount (%) |
|---|---|---|
| Nicotine | 1.08 | 18.5 |
| Water | 0.44 | 7.5 |
| Resin | 4.32 | 74.0 |
| Total | 5.84 | 100.0 |

Nicotine:resin ratio: 1:4 (0.25)
% water in obtained nicotine-resin composition: 7.5
The total process time was 20 minutes.

Example 2D—Nicotine Premix IV—Resin

A 60 liter planetary BEAR VARIMIXER mixer was charged with water, and nicotine was weighed and added. The mixer was stirred at low speed for 1 minute at ambient temperature. Then ion exchange resin AMBERLITE® IRP64 was weighed and added to the mixer. The mixer was closed, stirred at high speed for 5 minutes, opened and scraped down, if necessary. Finally, the mixer was stirred for further 5 minutes at high speed.

Thereby, a mixture of nicotine and cation exchange resin was produced from the constituents stated in the below table 4.

TABLE 4

Ingredients used to manufacture nicotine premix IV.

| Constituent | Amount (kg) | Amount (%) |
|---|---|---|
| Nicotine | 1.08 | 10.0 |
| Water | 5.40 | 50.0 |
| Resin | 4.32 | 40.0 |
| Total | 10.8 | 100.0 |

Nicotine:resin ratio: 1:4 (0.25)
% water in obtained nicotine-resin composition: 50.0
The total process time was 20 minutes.

Example 2E—Nicotine Premix V—Resin

A 60 liter planetary BEAR VARIMIXER mixer was charged with water, and nicotine was weighed and added. The mixer was stirred at low speed for 1 minute at ambient temperature. Then ion exchange resin AMBERLITE® IRP64 was weighed and added to the mixer. The mixer was closed, stirred at high speed for 5 minutes, opened and scraped down, if necessary. Finally, the mixer was stirred for further 5 minutes at high speed.

Thereby, a mixture of nicotine and cation exchange resin was produced from the constituents stated in the below table 4B.

TABLE 4B

Ingredients used to manufacture nicotine premix V.

| Constituent | Amount (kg) | Amount (%) |
|---|---|---|
| Nicotine | 1.78 | 20.0 |
| Water | 2.80 | 31.5 |
| Resin | 4.32 | 48.5 |
| Total | 8.90 | 100.0 |

Nicotine:resin ratio: 1:2.43 (0.41)
% water in obtained nicotine-resin composition: 31.5
The total process time was 20 minutes.

Example 2F—Nicotine Premix VI—Resin

A 60 liter planetary BEAR VARIMIXER mixer was charged with water, and nicotine was weighed and added. The mixer was stirred at low speed for 1 minute at ambient temperature. Then ion exchange resin AMBERLITE® IRP64 was weighed and added to the mixer. The mixer was closed, stirred at high speed for 5 minutes, opened and scraped down, if necessary. Finally, the mixer was stirred for further 5 minutes at high speed.

Thereby, a mixture of nicotine and cation exchange resin was produced from the constituents stated in the below table 4C.

TABLE 4C

Ingredients used to manufacture nicotine premix VI.

| Constituent | Amount (kg) | Amount (%) |
|---|---|---|
| Nicotine | 3.05 | 30.0 |
| Water | 2.80 | 27.5 |
| Resin | 4.32 | 42.5 |
| Total | 10.17 | 100.0 |

Nicotine:resin ratio: 1:1.4 (0.71)
% water in obtained nicotine-resin composition: 27.5
The total process time was 20 minutes.

Example 2G—Nicotine Premix VII—Resin

A 60 liter planetary BEAR VARIMIXER mixer was charged with water, and nicotine was weighed and added. The mixer was stirred at low speed for 1 minute at ambient temperature. Then ion exchange resin AMBERLITE® IRP64 was weighed and added to the mixer. The mixer was closed, stirred at high speed for 5 minutes, opened and scraped down, if necessary. Finally, the mixer was stirred for further 5 minutes at high speed.

Thereby, a mixture of nicotine and cation exchange resin was produced from the constituents stated in the below table 4D.

TABLE 4D

Ingredients used to manufacture nicotine premix VII.

| Constituent | Amount (kg) | Amount (%) |
|---|---|---|
| Nicotine | 5.15 | 42.0 |
| Water | 2.80 | 22.8 |
| Resin | 4.32 | 35.2 |
| Total | 12.27 | 100.0 |

Nicotine:resin ratio: 1.19:1 (1.19)
% water in obtained nicotine-resin composition: 22.8
The total process time was 20 minutes.

Example 2H—Nicotine Premix VIII—Resin

A 60 liter planetary BEAR VARIMIXER mixer was charged with water, and nicotine was weighed and added. The mixer was stirred at low speed for 1 minute at ambient temperature. Then ion exchange resin AMBERLITE® IRP64 and fiber were weighed and added to the mixer. The mixer was closed, stirred at high speed for 5 minutes, opened and scraped down, if necessary. Finally, the mixer was stirred for further 5 minutes at high speed.

Thereby, a mixture of nicotine and cation exchange resin was produced from the constituents stated in the below table 4E.

TABLE 4E

Ingredients used to manufacture nicotine premix VIII.

| Constituent | Amount (kg) | Amount (%) |
|---|---|---|
| Nicotine | 5.15 | 39.8 |
| Water | 2.80 | 21.6 |
| Resin | 4.32 | 33.4 |
| Pea fiber | 0.67 | 5.2 |
| Total | 12.94 | 100.0 |

Nicotine:resin ratio: 1.19:1 (1.19)
% water in obtained nicotine-resin composition: 21.6
The total process time was 20 minutes Example 3A—Pouches Pouches PPC1-PPC5 containing nicotine premix are prepared comprising powdered compositions as outlined in table 5. The pouches are made as follows.

Fibers and water are mixed using a planetary BEAR VARIMIXER mixer for 5 minutes. Then, the following ingredients were added subsequently under continuous mixing: Nicotine premix (mixed for 2 minutes), then the remaining ingredients except liquid flavor and glidant if any (mixed for 2 minutes), then liquid flavor if any (mixed for 1 minute), then glidant if any (mixed for 1 minute). The total mixing time is 9-11 minutes.

The final powder composition is filled into pouches (target fill weight 500 mg powder per pouch). The pouch material of example 1A, made from long fiber paper, is used. The powder is filled into pouches and is maintained in the pouch by a sealing.

The material of the pouches is heat sealable non-woven cellulose, such as long fiber paper. Pouches that are not in form of non-woven cellulose fabric may also be used according to the invention. The pouch material of example 1B may also be used.

The powder is filled into pouches and is maintained in the pouch by a sealing.

The pouches PPC6-PPC7 containing nicotine as nicotine salt or nicotine polacrilex resin as outlined in table 5. The pouches are made as follows.

Fibers and water are mixed using a planetary BEAR VARIMIXER mixer for 5 minutes. Then, the following ingredients were added subsequently under continuous mixing: first Nicotine bitartratexH2O (NBT, nicotine content of 32.5%) or nicotine polacrilex resin (NPR, nicotine content of 15.9%) as applicable (mixed for 2 minutes), then the remaining ingredients except liquid flavor and glidant if any (mixed for 2 minutes), then liquid flavor if any (mixed for 1 minute), then glidant if any (mixed for 1 minute). The total mixing time is 9-11 minutes.

The final powder composition is filled into pouches (target fill weight 500 mg powder per pouch). The pouch material of example 1A, made from long fiber paper, is used. The powder is filled into pouches and is maintained in the pouch by a sealing.

The material of the pouches is heat sealable non-woven cellulose, such as long fiber paper. Pouches that are not in form of non-woven cellulose fabric may also be used according to the invention. The pouch material of example 1B may also be used.

The powder is filled into pouches and is maintained in the pouch by a sealing.

TABLE 5

The nicotine premix II (example 2B) comprises 34.1 wt % water, thereby contributing to the total water content.

| PPC | PPC1 | PPC2 | PPC3 | PPC4 | PPC5 | PPC6 | PPC7 |
|---|---|---|---|---|---|---|---|
| Amount of nicotine | 9.6 mg | 9.6 mg | 9.6 mg | 9.6 mg | 9.6 mg | 9.6 mg | 9.6 mg |
| Water content [wt %] | 30 | 25 | 15 | 10 | 40 | 30 | 30 |
| Raw material | Content in weight percent | | | | | | |
| NPR | — | — | — | — | — | — | 12.1 |
| NBT | — | — | — | — | — | 5.9 | — |
| Nicotine premix II | 14.6 | 14.6 | 14.6 | 14.6 | 14.6 | — | — |
| Xylitol | 11.3 | 16.3 | 26.3 | 31.3 | 1.3 | 15.0 | 8.8 |
| Purified water | 25 | 20 | 10 | 5 | 35 | 30 | 30 |
| Wheat fiber | 30 | 30 | 30 | 30 | 30 | 30 | 30 |
| Sodium alginate | 2.0 | 2.0 | 2.0 | 2.0 | 2.0 | 2.0 | 2.0 |
| Sodium carbonate | 5.0 | 5.0 | 5.0 | 5.0 | 5.0 | 5.0 | 5.0 |
| Flavor | 8.9 | 8.9 | 8.9 | 8.9 | 8.9 | 8.9 | 8.9 |
| NaCl | 0.1 | 0.1 | 0.1 | 0.1 | 0.1 | 0.1 | 0.1 |
| High intensity sweetener | 1.0 | 1.0 | 1.0 | 1.0 | 1.0 | 1.0 | 1.0 |
| Potassium sorbate | 0.1 | 0.1 | 0.1 | 0.1 | 0.1 | 0.1 | 0.1 |
| Silicon dioxide | 2.0 | 2.0 | 2.0 | 2.0 | 2.0 | 2.0 | 2.0 |
| Total | 100 | 100 | 100 | 100 | 100 | 100 | 100 |

Pouch content: 500 mg total, i.e. nicotine concentration 19.2 mg/g

The Xylitol applied is e.g. trade name "XYLITAB 200".

Wheat fiber, trade name "VITACEL 600 WF plus". Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, apple fibers, bran fibers, bamboo fibers, powdered cellulose, cocoa fibers, and cellulose fiber.

For example, a mixture of e.g. menthol and peppermint may be used. Of course, other flavors as described herein may be use as well, in combination with menthol and/or peppermint or replacing these.

Sodium alginate, glycerol and hydroxypropyl cellulose (HPC) may be used as humectants. Other humectants as described herein may also be used in combination with sodium alginate, glycerol or HPC or as an alternative.

Silicon dioxide is used as a glidant. Other possible glidants include e.g. magnesium stearate, starch and talc.

Sodium carbonate is used as an alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium may as an example be used as high intensity sweeteners. Other usable high intensity sweeteners described herein may be used in combination with or instead of acesulfame potassium.

Pouches PPC1-PPC5 show that different pouches having a water content of at least 10% by weight of the pouch composition can be made using free-base nicotine. Pouches PPC6 and PPC7 have a similar water content as PPC1, but uses nicotine salt and nicotine in complex with an ion exchange resin.

Example 3B—Pouches

Pouches PPC11-PPC15 and Comp. 1-2 containing nicotine premix are prepared comprising powdered compositions as outlined in table 6. The pouches are made as follows.

Fibers and powder ingredients (except glidants) are mixed using a planetary BEAR VARIMIXER mixer for 2 minutes. Then, Nicotine premix is added and mixed for 2 minutes. Water is then added and mixed for 5 minutes followed by liquid flavor (if any—mixed for 1 minute) and glidant (if any—mixed for 1 minute). The total mixing time is 9-11 minutes.

TABLE 6

The nicotine premix II comprises 34.1 wt % water, thereby contributing to the total water content.

| PPC | PPC 11 | PPC 12 | PPC13 | PPC 14 | PPC 15 | Comp. 1 | Comp. 2 |
|---|---|---|---|---|---|---|---|
| Amount of nicotine | 9.6 mg | 9.6 mg | 9.6 mg | 9.6 mg | 9.6 mg | 9.6 mg | 9.6 mg |
| Water content [wt %] | 30 | 25 | 15 | 10 | 35 | 50 | 5 |
| Raw material | Content in weight percent | | | | | | |
| Nicotine premix II | 14.6 | 14.6 | 14.6 | 14.6 | 14.6 | 14.6 | 14.6 |
| Isomalt | 11.3 | 22.3 | 44.3 | 55.3 | 0.3 | 25 | 60.3 |
| Purified water | 25 | 20 | 10 | 5 | 30 | 45 | 0 |
| Wheat fiber | 30 | 24 | 12 | 6 | 36 | — | 6 |
| Sodium alginate | 2.0 | 2.0 | 2.0 | 2.0 | 2.0 | 2.0 | 2.0 |
| Sodium carbonate | 5.0 | 5.0 | 5.0 | 5.0 | 5.0 | 5.0 | 5.0 |
| Flavor | 9.0 | 9.0 | 9.0 | 9.0 | 9.0 | 5.3 | 9.0 |
| High intensity sweetener | 1.0 | 1.0 | 1.0 | 1.0 | 1.0 | 1.0 | 1.0 |
| Potassium sorbate | 0.1 | 0.1 | 0.1 | 0.1 | 0.1 | 0.1 | 0.1 |
| Silicon dioxide | 2.0 | 2.0 | 2.0 | 2.0 | 2.0 | 2.0 | 2.0 |
| Total | 100 | 100 | 100 | 100 | 100 | 100 | 100 |

Pouch content: 500 mg total.

The applied Isomalt is e.g. GALENIQ 720.

Wheat fiber, trade name "VITACEL 600 WF plus". Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, bran fibers, bamboo fibers, powdered cellulose, apple fibers, cocoa fibers, and cellulose fiber.

For example, a mixture of e.g. menthol and peppermint may be used. Of course, other flavors as described herein may be use as well, in combination with menthol and/or peppermint or replacing these.

Sodium alginate, glycerol and hydroxypropyl cellulose (HPC) may be used as humectants. Other humectants as described herein may also be used in combination with sodium alginate, glycerol or HPC or as an alternative.

Silicon dioxide is used as a glidant. Other possible glidants include e.g. magnesium stearate, starch and talc.

Sodium carbonate is used as an alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium may as an example be used as high intensity sweeteners. Other usable high intensity sweeteners described herein may be used in combination with or instead of acesulfame potassium.

Pouches PPC11-PPC15 shows varying water content of at least 10% by weight of the pouch composition. The water content varies, but the ratio between the amount of added purified water and the amount of fibers remain constant.

Example 3C—Pouches

Pouches PPC21-PPC26 are prepared comprising powdered compositions as outlined in table 7 and are made similarly to pouches PPC11-PPC15 of example 3B.

TABLE 7

| PPC | PPC21 | PPC22 | PPC23 | PPC24 | PPC25 | PPC26 |
|---|---|---|---|---|---|---|
| Amount of nicotine | 9.6 mg | 9.6 mg | 9.6 mg | 9.6 mg | 9.6 mg | 9.6 mg |
| Water content [wt %] | 30 | 30 | 30 | 30 | 30 | 30 |
| Raw material | Content in weight percent | | | | | |
| Nicotine premix II | 14.6 | 7.3 | 14.6 | 14.6 | 14.6 | 14.6 |
| Liquid nicotine* | — | 1.0 | — | — | — | — |
| Xylitol | 11.3 | 15.1 | 16.3 | 13.3 | 11.4 | 9.4 |
| Purified water | 25 | 27.5 | 25 | 25 | 25 | 25 |
| MCC (Avicel 102) | 30 | — | — | — | — | — |
| Wheat fiber | — | 30 | 30 | 30 | 30 | 30 |
| Sodium alginate | 2.0 | 2.0 | 2.0 | 2.0 | 2.0 | 2.0 |
| Sodium carbonate | 5.0 | 5.0 | — | 3.0 | 5.0 | 7.0 |
| Flavor | 9.0 | 9.0 | 9.0 | 9.0 | 9.0 | 9.0 |
| High intensity sweetener | 1.0 | 1.0 | 1.0 | 1.0 | 1.0 | 1.0 |
| Potassium sorbate | 0.1 | 0.1 | 0.1 | 0.1 | — | — |
| Silicon dioxide | 2.0 | 2.0 | 2.0 | 2.0 | 2.0 | 2.0 |
| Total | 100 | 100 | 100 | 100 | 100 | 100 |

*Liquid nicotine is added as a nicotine-sugar alcohol premix in powder form. The nicotine premix II comprises 34.1 wt % water, thereby contributing to the total water content.

Pouch content: 500 mg total.

Wheat fiber, trade name "VITACEL 600 WF plus". Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, bran fibers, bamboo fibers, powdered cellulose, apple fibers, cocoa fibers, and cellulose fiber.

For example, a mixture of e.g. menthol and peppermint may be used. Of course, other flavors as described herein may be use as well, in combination with menthol and/or peppermint or replacing these.

Sodium alginate, glycerol and hydroxypropyl cellulose (HPC) may be used as humectants. Other humectants as described herein may also be used in combination with sodium alginate, glycerol or HPC or as an alternative.

Silicon dioxide is used as a glidant. Other possible glidants include e.g. magnesium stearate, starch and talc.

Sodium carbonate is used as an alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium may as an example be used as high intensity sweeteners. Other usable high intensity sweeteners described herein may be used in combination with or instead of acesulfame potassium.

Pouch PPC21 shows the use of e.g. microcrystalline cellulose (MCC) instead of wheat fibers.

Pouch PPC22 shows the use of a combination of nicotine-ion exchange resin premix and nicotine-sugar alcohol premix.

Pouches PPC23-PPC26 shows the use of different amounts of buffering agent (here sodium carbonate). For high amounts of basic buffering agents, achieving a more alkaline environment, there is less need for a preservative (here potassium sorbate), therefore it is omitted in PPC25-PPC26, having the highest amounts of alkaline buffering agents.

Example 3D—Pouches

Pouches PPC31-PPC32 are prepared comprising powdered compositions as outlined in table 8 and are made similarly to pouches PPC1-PPC5 of example 3A, but using nicotine premix I and III, respectively.

Pouches PPC33-PPC37 are made as described below.

The nicotine and sugar alcohol (xylitol, sorbitol, maltitol or other) are weighed. The nicotine is slowly added to the sugar alcohol powder under stirring (KITCHENAID mixer operated at about 30 RPM in about 30 minutes).

The resulting granulate is sieved and placed on a tray. The resulting powder is dried at ambient temperature overnight and is thereafter sieved to obtain a nicotine-sugar alcohol premix. It is also possible to add an amount of water to the nicotine before mixing with the sugar alcohol. Any such water will then be evaporated during the drying.

Fibers and water are mixed using a planetary BEAR VARIMIXER mixer for 5 minutes. Then, the following ingredients were added subsequently under continuous mixing: Powder ingredients other than nicotine premix (mixed for 2 minutes), nicotine-sugar alcohol premix (mixed for 2 minutes), then liquid flavor if any (mixed for 1 minute) and finally glidant if any (mixed for 1 minute). The total mixing time is 9-11 minutes.

The final powder composition is filled into pouches (target fill weight 500 mg powder per pouch). The pouch material of example 1A, made from long fiber paper, is used. The powder is filled into pouches and is maintained in the pouch by a sealing.

The material of the pouches is heat sealable non-woven cellulose, such as long fiber paper. Pouches that are not in form of non-woven cellulose fabric may also be used according to the invention. The pouch material of example 1B may also be used.

The powder is filled into pouches and is maintained in the pouch by a sealing.

TABLE 8

| PPC | PPC31 | PPC32 | PPC33 | PPC34 | PPC35 | PPC36 | PPC37 |
|---|---|---|---|---|---|---|---|
| Amount of nicotine | 9.6 mg | 9.6 mg | 9.6 mg | 9.6 mg | 9.6 mg | 9.6 mg | 9.6 mg |
| Water content [wt %] | 30 | 30 | 30 | 30 | 30 | 30 | 30 |
| Raw material | Content in weight percent | | | | | | |
| Nicotine premix I | 33.7 | — | — | — | — | — | — |
| Nicotine premix III | — | 10.4 | — | — | — | — | — |
| Liquid nicotine* | — | — | 1.9 | 1.9 | 1.9 | 1.9 | 1.9 |
| Isomalt | 11.2 | 11.3 | 19.0 | — | — | — | — |
| Sorbitol | — | — | — | 19.0 | — | — | — |
| Maltitol | — | — | — | — | 19.0 | — | — |
| Inulin | — | — | — | — | — | 19.0 | — |
| Polydextrose | — | — | — | — | — | — | 19.0 |

TABLE 8-continued

| PPC | PPC31 | PPC32 | PPC33 | PPC34 | PPC35 | PPC36 | PPC37 |
|---|---|---|---|---|---|---|---|
| Purified water | 6 | 29.2 | 30 | 30 | 30 | 30 | 30 |
| Wheat fiber | 30 | 30 | 30 | 30 | 30 | 30 | 30 |
| Sodium alginate | 2.0 | 2.0 | 2.0 | 2.0 | 2.0 | 2.0 | 2.0 |
| Sodium carbonate | 5.0 | 5.0 | 5.0 | 5.0 | 5.0 | 5.0 | 5.0 |
| Flavor | 9.0 | 9.0 | 9.0 | 9.0 | 9.0 | 9.0 | 9.0 |
| High intensity sweetener | 1.0 | 1.0 | 1.0 | 1.0 | 1.0 | 1.0 | 1.0 |
| Potassium sorbate | 0.1 | 0.1 | 0.1 | 0.1 | 0.1 | 0.1 | 0.1 |
| Silicon dioxide | 2.0 | 2.0 | 2.0 | 2.0 | 2.0 | 2.0 | 2.0 |
| Total | 100 | 100 | 100 | 100 | 100 | 100 | 100 |

*Liquid nicotine is added as a nicotine-sugar alcohol premix or as a nicotine-water-soluble fiber premix in powder form. The nicotine premix I comprises 71.4 wt % water, thereby contributing to the total water content. The nicotine premix II comprises 34.1 wt % water, thereby contributing to the total water content. The nicotine premix III comprises 7.5 wt % water, thereby contributing to the total water content.

Pouch content: 500 mg total.

Wheat fiber, trade name "VITACEL 600 WF plus". Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, bran fibers, bamboo fibers, powdered cellulose, apple fibers, cocoa fibers, and cellulose fiber.

For example, a mixture of e.g. menthol and peppermint may be used. Of course, other flavors as described herein may be use as well, in combination with menthol and/or peppermint or replacing these.

Sodium alginate, glycerol and hydroxypropyl cellulose (HPC) may be used as humectants. Other humectants as described herein may also be used in combination with sodium alginate, glycerol or HPC or as an alternative.

Silicon dioxide is used as a glidant. Other possible glidants include e.g. magnesium stearate, starch and talc.

Sodium carbonate is used as an alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium may as an example be used as high intensity sweeteners. Other usable high intensity sweeteners described herein may be used in combination with or instead of acesulfame potassium.

Pouches PPC31-PPC32 show use of other nicotine premixes.

Pouches PPC33-PPC35 show use of nicotine pre-mixed with different sugar alcohol.

Pouches PPC36-PPC37 show use of nicotine pre-mixed with different water-soluble fibers.

Example 3E—Pouches

Pouches PPC41-PPC46 are prepared comprising powdered compositions as outlined in table 9 and are made similarly to pouches PPC1-PPC5 of example 3A.

TABLE 9

The nicotine premix II comprises 34.1 wt % water, thereby contributing to the total water content.

| PPC | PPC41 | PPC42 | PPC43 | PPC44 | PPC45 | PPC46 |
|---|---|---|---|---|---|---|
| Amount of nicotine | 4.8 mg | 7.2 mg | 9.6 mg | 12 mg | 9.6 mg | 9.6 mg |
| Water content [wt %] | 27.5 | 28.3 | 30 | 31.2 | 30 | 30 |
| Raw material | Content in weight percent | | | | | |
| Nicotine premix II | 7.3 | 9.7 | 14.6 | 18.3 | 14.6 | 14.6 |
| Xylitol | 18.6 | 16.2 | 11.3 | 7.6 | 13.3 | 5 |
| Erythritol | — | — | — | — | — | 6.3 |
| Purified water | 25 | 25 | 25 | 25 | 25 | 25 |
| Wheat fiber | 30 | 30 | 30 | 30 | 30 | 30 |
| Sodium alginate | 2.0 | 2.0 | 2.0 | 2.0 | — | 2.0 |
| Sodium carbonate | 5.0 | 5.0 | 5.0 | 5.0 | 5.0 | 5.0 |
| Flavor | 9.0 | 9.0 | 9.0 | 9.0 | 9.0 | 8.9 |
| NaCl | — | — | — | — | — | 0.1 |
| High intensity sweetener | 1.0 | 1.0 | 1.0 | 1.0 | 1.0 | 1.0 |
| Potassium sorbate | 0.1 | 0.1 | 0.1 | 0.1 | 0.1 | 0.1 |
| Silicon dioxide | 2.0 | 2.0 | 2.0 | 2.0 | 2.0 | 2.0 |
| Total | 100 | 100 | 100 | 100 | 100 | 100 |

Pouch content: 500 mg total.

Wheat fiber, trade name "VITACEL 600 WF plus". Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, bran fibers, bamboo fiber, powdered cellulose, apple fibers, cocoa fibers, and cellulose fiber.

For example, a mixture of e.g. menthol and peppermint may be used. Of course, other flavors as described herein may be use as well, in combination with menthol and/or peppermint or replacing these.

Silicon dioxide is used as a glidant. Other possible glidants include e.g. magnesium stearate, starch and talc.

Sodium alginate, glycerol and hydroxypropyl cellulose (HPC) may be used as humectants. Other humectants as described herein may also be used in combination with sodium alginate, glycerol or HPC or as an alternative.

Sodium carbonate is used as an alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium may as an example be used as high intensity sweeteners. Other usable high intensity sweeteners described herein may be used in combination with or instead of acesulfame potassium.

Pouches PPC41-PPC44 show use of different doses of nicotine, from 4.8 mg to 12 mg.

Pouch PPC45 shows pouch without alginate, otherwise comparable to pouch PPC43.

Pouch PPC46 shows a pouch with a combination of two sugar alcohols.

Example 3F—Pouches

Pouches PPC51-PPC53 are prepared comprising powdered compositions as outlined in table 10 and are made as follows.

Fibers and powder ingredients (except nicotine containing powders and glidants) are mixed for 1 minute using a planetary BEAR VARIMIXER mixer. Then, NPR and NBT is added and mixed for 2 minutes (if applicable). Nicotine premix is then added and mixed for 2 minutes. Subsequently, water is added and mixed for 5 minutes followed by liquid flavor (if any—mixed for 1 minute) and glidant (if any—mixed for 1 minute). The total mixing time is 9-11 minutes.

TABLE 10

The nicotine premix II comprises 34.1 wt % water, thereby contributing to the total water content.

| PPC | PPC51 | PPC52 | PPC53 |
|---|---|---|---|
| Amount of nicotine | 9.6 mg | 9.6 mg | 9.6 mg |
| Water content [wt %] | 30 | 30 | 30 |
| Raw material | Content in weight percent | | |
| NPR | — | 6.0 | 3.0 |
| NBT | 2.9 | — | 1.5 |
| Nicotine premix II | 7.3 | 7.3 | 7.3 |
| Isomalt | 15.2 | 12.1 | 13.6 |
| Purified water | 27.5 | 27.5 | 27.5 |
| Wheat fiber | 30 | 30 | 30 |
| Sodium carbonate | 5.0 | 5.0 | 5.0 |
| Flavor | 9.0 | 9.0 | 9.0 |
| High intensity sweetener | 1.0 | 1.0 | 1.0 |
| Potassium sorbate | 0.1 | 0.1 | 0.1 |
| Silicon dioxide | 2.0 | 2.0 | 2.0 |
| Total | 100 | 100 | 100 |

Pouch content: 500 mg total

Wheat fiber, trade name "VITACEL 600 WF plus". Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, bran fibers, bamboo fibers, powdered cellulose, apple fibers, cocoa fibers, and cellulose fiber.

For example, a mixture of e.g. menthol and peppermint may be used. Of course, other flavors as described herein may be use as well, in combination with menthol and/or peppermint or replacing these.

Silicon dioxide is used as a glidant. Other possible glidants include e.g. magnesium stearate, starch and talc.

Sodium carbonate is used as an alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium may as an example be used as high intensity sweeteners. Other usable high intensity sweeteners described herein may be used in combination with or instead of acesulfame potassium.

Pouch PPC51 shows pouch using nicotine-ion exchange resin premix in combination with nicotine bitartrate (NBT).

Pouch PPC52 shows pouch using nicotine-ion exchange resin premix in combination with nicotine polacrilex resin (NPR).

Pouch PPC53 shows pouch using nicotine-ion exchange resin premix in combination with nicotine bitartrate (NBT) and nicotine polacrilex resin (NPR).

Example 3G—Pouches

Pouches PPC61-PPC63 and COMP.P3 containing nicotine premix are prepared comprising powdered compositions as outlined in table 11. The pouches are made as follows.

Powdered ingredients including powdered flavor (if any) are mixed using a planetary BEAR VARIMIXER mixer for 2 minutes. Then, the nicotine is added and mixed for 2 minutes. Then water is slowly added while the mixer is running, followed by addition of liquid flavor. Finally, silicon dioxide is added and the mixed for about 1 minute. The total mixing time is about 30 minutes.

The final powder composition is filled into pouches (target fill weight 500 mg powder per pouch). The pouch material of example 1A, made from long fiber paper, is used. The powder is filled into pouches and is maintained in the pouch by a sealing.

The material of the pouches is heat sealable non-woven cellulose, such as long fiber paper. Pouches that are not in form of non-woven cellulose fabric may also be used according to the invention. The pouch material of example 1B may also be used.

The powder is filled into pouches and is maintained in the pouch by a sealing.

TABLE 11

The nicotine premix II comprises 34.1 wt % water, thereby contributing to the total water content.

| PPC | PPC61 | PPC62 | PPC63 | COMP. P3 |
|---|---|---|---|---|
| Amount of nicotine | 9.6 mg | 9.6 mg | 9.6 mg | 9.6 mg |
| Water content [wt %] | 15 | 30 | 45 | 5 |
| Density (gram per Liter) | 256 | 303 | 578 | ND |
| Hausner ratio | 1.25 | 1.22 | 1.11 | ND |
| Raw material | Content in weight percent | | | |
| Nicotine premix II | 14.6 | 14.6 | 14.6 | 14.6 |
| Sugar alcohol(s) | 12.3 | 12.3 | 12.3 | 12.3 |
| Purified water | 10 | 25 | 40 | — |
| Wheat fiber | 45 | 30 | 15 | 55 |
| Sodium alginate | 2.0 | 2.0 | 2.0 | 2.0 |
| Sodium carbonate | 4.0 | 4.0 | 4.0 | 4.0 |
| Flavor | 9.0 | 9.0 | 9.0 | 9.0 |
| High intensity sweetener | 1.0 | 1.0 | 1.0 | 1.0 |
| Potassium sorbate | 0.1 | 0.1 | 0.1 | 0.1 |
| Silicon dioxide | 2.0 | 2.0 | 2.0 | 2.0 |
| Total | 100 | 100 | 100 | 100 |

Pouch content: 500 mg total, i.e. nicotine concentration 19.2 mg/g

The sugar alcohol(s) may be Xylitol e.g. trade name "XYLITAB 200" and/or Isomalt e.g. tradename "GALENIQ 720".

Wheat fiber, trade name "VITACEL 600 WF plus". Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, bran fibers, bamboo fibers, powdered cellulose, apple fibers, cocoa fibers, and cellulose fiber.

For example, a mixture of e.g. menthol and peppermint may be used. Of course, other flavors as described herein may be use as well, in combination with menthol and/or peppermint or replacing these.

by liquid flavor (if any—mixed for 15 minutes) and glidant (if any—mixed for 1 minute). The total mixing time is 19-35 minutes.

The final powder composition is filled into pouches (target fill weight 500 mg powder per pouch). The pouch material of example A, made from long fiber paper, is used. The powder is filled into pouches and is maintained in the pouch by a sealing. The pouch material of example 1B may also be used.

TABLE 12

The nicotine premixes comprise water in varying amount, thereby contributing to the total water content.

| PPC | PPC 71 | PPC 72 | PPC 73 | PPC 74 | PPC 75 | PPC 76 | PPC 77 |
|---|---|---|---|---|---|---|---|
| Amount of nicotine | 9.6 mg | 9.6 mg | 9.6 mg | 9.6 mg | 9.6 mg | 9.6 mg | 9.6 mg |
| Water content [wt %] | 30 | 30 | 30 | 30 | 30 | 30 | 30 |
| Raw material | Content in weight percent | | | | | | |
| Nicotine premix IV | 19.2 | — | — | — | — | — | — |
| Nicotine premix V | — | 9.6 | — | — | — | — | — |
| Nicotine premix VI | — | — | — | — | 6.4 | 6.4 | 6.4 |
| Nicotine premix VII | — | — | 4.6 | — | — | — | — |
| Nicotine premix VIII | — | — | — | 4.8 | — | — | — |
| Purified water | 21 | 27 | 29 | 29 | 28 | 28 | 28 |
| Wheat fiber | 30 | 30 | 30 | 29.75 | — | — | — |
| Oat fiber | — | — | — | — | 30 | — | — |
| Pea fiber | — | — | — | 0.25 | — | 30 | — |
| Powdered cellulose | — | — | — | — | — | — | 30 |
| Xylitol DC | 5.0 | 5.0 | 5.0 | 5.0 | 5.0 | 5.0 | 5.0 |
| Erythritol | 7.7 | 11.3 | 14.3 | 14.1 | 13.5 | 13.5 | 13.5 |
| Sodium alginate | 2.0 | 2.0 | 2.0 | 2.0 | 2.0 | 2.0 | 2.0 |
| Sodium carbonate | 5.0 | 5.0 | 5.0 | 5.0 | 5.0 | 5.0 | 5.0 |
| Flavor | 7.0 | 7.0 | 7.0 | 7.0 | 7.0 | 7.0 | 7.0 |
| High intensity sweetener | 1.0 | 1.0 | 1.0 | 1.0 | 1.0 | 1.0 | 1.0 |
| Potassium sorbate | 0.1 | 0.1 | 0.1 | 0.1 | 0.1 | 0.1 | 0.1 |
| Silicon dioxide | 2.0 | 2.0 | 2.0 | 2.0 | 2.0 | 2.0 | 2.0 |
| Total | 100 | 100 | 100 | 100 | 100 | 100 | 100 |

Sodium alginate, glycerol and hydroxypropyl cellulose (HPC) may be used as humectants. Other humectants as described herein may also be used in combination with sodium alginate, glycerol or HPC or as an alternative.

Silicon dioxide is used as a glidant. Other possible glidants include e.g. magnesium stearate, starch and talc.

Sodium carbonate is used as an alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium may as an example be used as high intensity sweeteners. Other usable high intensity sweeteners described herein may be used in combination with or instead of acesulfame potassium.

Pouches PPC61-PPC63 show pouches having different water and water-insoluble fiber contents.

Example 3H—Pouches

Pouches PPC71-PPC76 containing nicotine premix are prepared comprising powdered compositions as outlined in table 12. The pouches are made as follows.

Fibers and powder ingredients (except glidants) are mixed using a Lödige mixer for 2 minutes. Then, Nicotine premix is added and mixed for 2 minutes. With the mixer running, water is then added during a period of 15 minutes followed Nicotine premix VIII comprises peafiber.
Pouch content: 500 mg total, i.e. nicotine conc 19.2 mg/g
Wheat fiber, trade name "VITACEL 600 WF plus".
Powdered cellulose, trade name "VITACEL L00" or "VITACEL L700G".
Oat fiber, trade name "VITACEL HF 600".
Pea fiber, trade name "VITACEL EF150".

Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, apple fibers, cocoa fibers, bamboo fibers, powdered cellulose, bran fibers, and cellulose fiber.

For example, a mixture of e.g. menthol and peppermint may be used. Of course, other flavors as described herein may be use as well, in combination with menthol and/or peppermint or replacing these.

Silicon dioxide is used as a glidant. Other possible glidants include e.g. magnesium stearate, starch and talc.

Sodium alginate, glycerol and hydroxypropyl cellulose (HPC) may be used as humectants. Other humectants as described herein may also be used in combination with sodium alginate, glycerol or HPC or as an alternative.

Sodium carbonate and sodium bicarbonate are used as alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium and/or sucralose may as an example be used as high intensity sweeteners. Other usable high intensity sweeteners described herein may be used in combination with or instead of acesulfame potassium and/or sucralose.

Pouches PPC71-PPC74 show use of different nicotine premixes.

Pouches PPC75-PPC77 show use of different fibers.

Example 3I—Pouches

Pouches PPC81-PPC92 containing nicotine premix are prepared comprising powdered compositions as outlined in table 13-1 and 13-11. The pouches are made as follows.

Fibers and powder ingredients (except glidants) are mixed using a LOEDIGE mixer for 2 minutes. Then, Nicotine premix is added and mixed for 2 minutes. With the mixer running, water is then added during a period of 15 minutes followed by liquid flavor (if any—mixed for 15 minutes) and glidant (if any—mixed for 1 minute). The total mixing time is 19-35 minutes.

The final powder composition is filled into pouches (target fill weight 500 mg powder per pouch). The pouch material of example 1A, made from long fiber paper, is used. The powder is filled into pouches and is maintained in the pouch by a sealing. The pouch material of example 1B may also be used.

TABLE 13-I

| PPC | PPC 81 | PPC 82 | PPC 83 | PPC 84 | PPC 85 | PPC 86 | PPC 87 | PPC 88 |
|---|---|---|---|---|---|---|---|---|
| Amount of nicotine | 9.6 mg | 9.6 mg | 9.6 mg | 9.6 mg | 9.6 mg | 9.6 mg | 9.6 mg | 9.6 mg |
| Water content [wt %] | 30 | 30 | 30 | 30 | 30 | 30 | 30 | 30 |
| Raw material | Content in weight percent | | | | | | | |
| Nicotine premix II | 14.6 | 14.6 | 14.6 | 14.6 | — | — | — | — |
| Nicotine premix VI | — | — | — | — | 6.4 | 6.4 | 6.4 | 6.4 |
| Purified water | 25 | 25 | 25 | 25 | 28 | 28 | 28 | 28 |
| Wheat fiber | 30 | — | — | — | — | — | — | 15 |
| Oat fiber | — | 30 | — | — | 15 | — | — | — |
| Pea fiber | — | — | 30 | — | — | 15 | — | — |
| Powdered cellulose | — | — | — | 30 | — | — | 15 | — |
| Xylitol DC | 5.0 | 5.0 | 5.0 | 5.0 | 5.0 | 5.0 | 5.0 | 5.0 |
| Erythritol | 8.3 | 8.3 | 8.3 | 8.3 | 28.5 | 28.5 | 28.5 | 28.5 |
| Sodium alginate | 2.0 | 2.0 | 2.0 | 2.0 | 2.0 | 2.0 | 2.0 | 2.0 |
| Sodium carbonate | 5.0 | 5.0 | 5.0 | 5.0 | 5.0 | 5.0 | 5.0 | 5.0 |
| Flavor | 7.0 | 7.0 | 7.0 | 7.0 | 7.0 | 7.0 | 7.0 | 7.0 |
| High intensity sweetener | 1.0 | 1.0 | 1.0 | 1.0 | 1.0 | 1.0 | 1.0 | 1.0 |
| Potassium sorbate | 0.1 | 0.1 | 0.1 | 0.1 | 0.1 | 0.1 | 0.1 | 0.1 |
| Silicon dioxide | 2.0 | 2.0 | 2.0 | 2.0 | 2.0 | 2.0 | 2.0 | 2.0 |
| Total | 100 | 100 | 100 | 100 | 100 | 100 | 100 | 100 |

TABLE 13-II

| PPC | PPC 89 | PPC 90 | PPC 91 | PPC 92 | PPC 93 | PPC 94 |
|---|---|---|---|---|---|---|
| Amount of nicotine | 9.6 mg | 9.6 mg | 9.6 mg | 9.6 mg | 9.6 mg | 9.6 mg |
| Water content [wt %] | 30 | 30 | 30 | 30 | 30 | 30 |
| Raw material | Content in weight percent | | | | | |
| Nicotine premix II | 14.6 | 14.6 | 14.6 | 14.6 | — | — |
| Nicotine premix VI | — | — | — | — | 6.4 | 6.4 |
| Purified water | 25 | 25 | 25 | 25 | 28 | 28 |
| Wheat fiber | 15 | — | — | — | 15 | 15 |
| Oat fiber | — | 15 | — | — | — | — |
| Pea fiber | — | — | 15 | — | — | — |
| Powdered cellulose | — | — | — | 15 | — | — |
| Xylitol DC | 5.0 | 5.0 | 5.0 | 5.0 | 5.0 | 5.0 |
| Erythritol | 23.3 | 23.3 | 23.3 | 23.3 | 28.5 | 20.5 |
| Sodium alginate | 2.0 | 2.0 | 2.0 | 2.0 | — | — |
| NaCl | — | — | — | — | — | 10 |
| Sodium carbonate | 5.0 | 5.0 | 5.0 | 5.0 | 3.5 | 5.0 |
| Sodium bicarbonate | — | — | — | — | 3.5 | — |
| Flavor | 7.0 | 7.0 | 7.0 | 7.0 | 7.0 | 7.0 |
| High intensity sweetener | 1.0 | 1.0 | 1.0 | 1.0 | 1.0 | 1.0 |
| Potassium sorbate | 0.1 | 0.1 | 0.1 | 0.1 | 0.1 | 0.1 |
| Silicon dioxide | 2.0 | 2.0 | 2.0 | 2.0 | 2.0 | 2.0 |
| Total | 100 | 100 | 100 | 100 | 100 | 100 |

The nicotine premixes comprise water in varying amount, thereby contributing to the total water content.

Pouch content: 500 mg total, i.e. nicotine conc 19.2 mg/g

Wheat fiber, trade name "VITACEL 600 WF plus" or "VITACEL 200WF".

Powdered cellulose, trade name "VITACEL L00" or "VITACEL L700G".

Oat fiber, trade name "VITACEL HF 600".

Pea fiber, trade name "VITACEL EF150".

Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, apple fibers, cocoa fibers, bamboo fibers, powdered cellulose, bran fibers, and cellulose fiber.

For example, a mixture of e.g. menthol and peppermint may be used. Of course, other flavors as described herein may be use as well, in combination with menthol and/or peppermint or replacing these.

Silicon dioxide is used as a glidant. Other possible glidants include e.g. magnesium stearate, starch and talc.

Sodium alginate, glycerol and hydroxypropyl cellulose (HPC) may be used as humectants. Other humectants as described herein may also be used in combination with sodium alginate, glycerol or HPC or as an alternative.

Sodium carbonate and sodium bicarbonate are used as alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium and/or sucralose may as an example be used as high intensity sweeteners. Other usable high intensity sweeteners described herein may be used in combination with or instead of acesulfame potassium and/or sucralose.

Pouches PPC81-PPC92 shows the use of different fibers, in different amounts and with different nicotine premixes.

Pouches PPC93-PPC94 show use of buffer pair and higher amount of salt, respectively.

Example 3J—Pouches

Pouches PPC101-PPC107 containing nicotine premix are prepared comprising powdered compositions as outlined in table 14. The pouches are made as follows.

Fibers and powder ingredients (except glidants) are mixed using a Lödige mixer for 2 minutes. Then, Nicotine premix is added and mixed for 2 minutes. With the mixer running, water is then added during a period of 15 minutes followed by liquid flavor (if any—mixed for 15 minutes) and glidant (if any—mixed for 1 minute). The total mixing time is 19-35 minutes.

Sodium alginate, glycerol and hydroxypropyl cellulose (HPC) may be used as humectants. Other humectants as described herein may also be used in combination with sodium alginate, glycerol or HPC or as an alternative.

Sodium carbonate and sodium bicarbonate are used as alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium and/or sucralose may as an example be used as high intensity sweeteners. Other usable high intensity sweeteners described herein may be used in combination with or instead of acesulfame potassium and/or sucralose.

Pouches PPC101-PPC102 show use of different sweetener and buffer combinations.

Pouches PPC103-PPC104 show pouches with varying fiber content.

Pouches PPC105-PPC107 show use of different humectants.

Example 3K—Release Test (In Vivo)

The release properties of the pouches were evaluated by a panel of assessors, preferably at least 8 assessors. Each assessor was provided with a pouch to place in the oral cavity, specifically at the upper lip.

TABLE 14

The nicotine premix VI comprises 27.5 wt % water, thereby contributing to the total water content.

| PPC | PPC 101 | PPC 102 | PPC 103 | PPC 104 | PPC 105 | PPC 106 | PPC 107 |
|---|---|---|---|---|---|---|---|
| Amount of nicotine | 9.6 mg | 9.6 mg | 9.6 mg | 9.6 mg | 9.6 mg | 9.6 mg | 9.6 mg |
| Water content [wt %] | 30 | 30 | 30 | 30 | 30 | 30 | 30 |
| Raw material | Content in weight percent | | | | | | |
| Nicotine premix VI | 6.4 | 6.4 | 6.4 | 6.4 | 6.4 | 6.4 | 6.4 |
| Xylitol | 5 | 18.3 | 18.3 | 18.3 | 5 | 5 | 5 |
| Erythritol | 13.5 | — | — | — | 13.5 | 13.5 | 13.5 |
| Purified water | 28 | 28 | 28 | 28 | 28 | 28 | 28 |
| Wheat fiber | 30 | 30 | 20 | 40 | 30 | 30 | 30 |
| Sodium alginate | 2.0 | 2.0 | 2.0 | 2.0 | 2.0 | — | — |
| Glycerol | — | — | — | — | — | 2.0 | — |
| Hydroxypropyl cellulose | — | — | — | — | — | — | 2.0 |
| Sodium carbonate | 5.0 | 3.0 | 3.0 | 3.0 | 3.0 | 3.0 | 3.0 |
| Sodium bicarbonate | — | 2.0 | 2.0 | 2.0 | 2.0 | 2.0 | 2.0 |
| Flavor | 7.0 | 7.0 | 7.0 | 7.0 | 7.0 | 7.0 | 7.0 |
| High intensity sweetener | 1.0 | 1.0 | 1.0 | 1.0 | 1.0 | 1.0 | 1.0 |
| Potassium sorbate | 0.1 | 0.1 | 0.1 | 0.1 | 0.1 | 0.1 | 0.1 |
| Silicon dioxide | 2.0 | 2.0 | 2.0 | 2.0 | 2.0 | 2.0 | 2.0 |
| Total | 100 | 100 | 100 | 100 | 100 | 100 | 100 |

Pouch content: 500 mg total.

Wheat fiber, trade name "VITACEL 600 WF plus". Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, apple fibers, powdered cellulose, cocoa fibers, bamboo fibers, bran fibers, and cellulose fiber.

For example, a mixture of e.g. menthol and peppermint may be used. Of course, other flavors as described herein may be use as well, in combination with menthol and/or peppermint or replacing these.

Silicon dioxide is used as a glidant. Other possible glidants include e.g. magnesium stearate, starch and talc.

Pouch was removed from the oral cavity of the test person after 2 min., 5 min., 10 min., 30 min. or 60 min.

The amount of remaining nicotine in the pouches were determined using standard HPLC techniques.

Two pouches were tested for each timepoint. The average of the result obtained for each timepoint was used to make profiles of the nicotine content in the pouches over time.

The amount of released nicotine could thereafter be obtained by subtracting the remaining amount of nicotine in the pouch from the initial dosage of nicotine in the tested pouch.

Example 3L—Release Test (In Vitro)

The release properties of the pouches were tested in an in vitro experiment.

Individual pouches were put into reaction tubes having a diameter approx. 2 cm and containing 10 mL of 0.02 M potassium dihydrogen phosphate-buffer (pH adjusted to 7.4) at warmed to 37 degrees Celsius.

No stirring or shaken was applied during the release experiment.

Pouches were removed from the buffer after 2 min., 5 min., 10 min., 30 min. or 60 min. Excess buffer was removed, and the amount of remaining nicotine were determined using standard HPLC.

Two pouches were tested for each timepoint. The average of the result obtained for each timepoint was used to make profiles of the nicotine content in the pouches over time.

The amount of released nicotine could thereafter be obtained by subtracting the remaining amount of nicotine in the pouch from the initial dosage of nicotine in the tested pouch.

Example 3M—Content Uniformity

Content Uniformity (CU) of a pouch sample was determined by analysis of 10 replicate sub-samples. For each sub-sample of approx. 500 mg, the content of nicotine was determined using standard HPLC techniques.

The nicotine content of a sub-sample was expressed as a percentage relative to the nominal content of nicotine in the sample (i.e. % Label Claim). For example, a pouch sample with a nominal content of nicotine of 20 mg/g being analyzed to have an actual content of 19 mg/g would have a nicotine content of 95% Label Claim.

The Content Uniformity of the sample is then determined as the Relative Standard Deviation (RSD) of the individual analyses of relative nicotine content in the 10 replicates.

Example 4—Evaluation

The produced pouches of the invention were evaluated and found highly suitable as delivery vehicles of nicotine in that they provide a favorable release of nicotine and at the same time are pleasant to the user, e.g. with respect to a desirable sticky texture. In particular, the pouches of the invention did not need any wetting before use as opposed to conventional nicotine pouches with low moisture content which may feel dry initially in use.

Example 5—Mobility and Density

The pouches PPC1 and PPC46 were compared to the Comp. 1 pouch with respect to mobility and density.

Angle of repose was measured for PPC61-PPC63. PPC63 had a water content that is 15% larger than PPC62, which again had a water content 15% larger than PPC61. However, the difference between angle of repose for PPC63 and PPC62 was significantly greater than the difference between PPC62 and PPC61.

The pouch compositions of pouches PPC1 and PPC46 were found to have a much higher mobility and were processable in a pouch packaging machine.

Also, pouches PPC1 and PPC46 were found to have a significantly lower density of the pouch compositions in the finished pouches, while having a high degree of filling.

Example 6—Degree of Filling

To evaluate the influence of the degree of filling, a number of pouches were made using the same pouch composition, PPC62. The degree of filling was checked by comparing weight with a full pouch (100%). Each pouch was evaluated whether it was perceived to be satisfactory filled. This evaluation was made first by feeling the pouch by hands, then by inserting the pouch to the mouth. Each pouch is assigned approved or disapproved rating for hand feeling and oral feeling.

TABLE 15

Measured filling degree of pouches with pouch composition PPC 62. "Appr." denotes approved rating, whereas "Not A" denotes not approved rating.

| | Degree of filling | | | | | | |
|---|---|---|---|---|---|---|---|
| | 50 | 60 | 65 | 70 | 75 | 80 | 100 |
| Hand evaluation | Not A | Not A | Appr. | Appr. | Appr. | Appr. | Appr. |
| Mouth evaluation | Not A | Not A | Not A | Appr. | Appr. | Appr. | Appr. |

As can be seen from table 15, pouches being at least 65% filled gives an approved rating for feeling in the hand, whereas pouches being at least 70% filled gives an approved rating for feeling in the mouth.

Example 7—Degree of Filling and Water Content

To evaluate how the content of water influence users preference for degree of filling, a number of pouches were made using pouch compositions with varying water content, PPC61, PPC62 (see results above) and COMP.P3.

The degree of filling was checked by comparing weight with a full pouch (100%). Each pouch was evaluated whether it was perceived to be satisfactory filled. This evaluation was made first by feeling the pouch by hands, then by inserting the pouch to the mouth. Each pouch is assigned approved or disapproved rating for hand feeling and oral feeling.

TABLE 16

Measured filling degree of pouches with pouch composition PPC 61 and COMP. P3. "Appr."denotes approved rating, whereas "Not A" denotes not approved rating.

| PPC | | Degree of filling | | | | | | |
|---|---|---|---|---|---|---|---|---|
| (water content) | | 50 | 55 | 60 | 65 | 75 | 80 | 100 |
| COMP. P3 (5%) | Hand evaluation | Not A | Not A | Not A | Appr. | Appr. | Appr. | Appr. |
| | Mouth evaluation | Not A | Not A | Not A | Not A | Appr. | Appr. | Appr. |
| PPC61 (15%) | Hand evaluation | Not A | Not A | Appr. | Appr. | Appr. | Appr. | Appr. |
| | Mouth evaluation | Not A | Not A | Appr. | Appr. | Appr. | Appr. | Appr. |

As can be seen from table 16, pouches containing 5% water and being at least 65% filled gives an approved rating for feeling in the hand, whereas pouches containing 15% water gives an approved rating for feeling in the hand already when being at least 60% filled.

Pouches containing 5% water and being at least 75% filled gives an approved rating for feeling in the mouth, whereas pouches containing 15% water gives an approved rating for feeling in the mouth already when being at least 60% filled.

Example 8—User Evaluation

The pouch product PPC1 was evaluated with respect to perceived effect from nicotine and with respect to burning (tingling) sensation.

Evaluation of perceived effect from nicotine and burning (tingling) sensation is performed as described in the following.

Perceived effect from nicotine and burning (tingling) sensation was evaluated by a test panel of 4 trained assessors. Each assessor evaluates all samples twice. Average evaluations are estimated.

The pouch product PPC1 was evaluated to have a fast onset of action and a high perceived effect from nicotine by all four assessors. Also, all four assessors evaluated the pouch product PPC1 to have a high burning (tingling) sensation.

Similarly, the pouch product PPC1 was evaluated with respect to perceived effect from nicotine in the same way as described above. The pouch product PPC1 was evaluated to have a high perceived effect from nicotine by all four assessors.

Example 9—Release Results

Pouches were exposed to the in vitro release experiment described in example 3L.

TABLE 17

In vitro release results.

| PPC | Fiber | Remaining nicotine in pouch after 2 min | Remaining nicotine in pouch after 10 min | Release rate in time period: 2-10 min (% per min.) |
|---|---|---|---|---|
| PPC82 | Oat (HF 600) | 74.7% | 67.9% | 0.85 |
| PPC81 | Wheat (WF600) | 80.0% | 71.6% | 1.05 |
| PPC84 | Cellulose L00 | 66.6% | 62% | 0.58 |
| PPC83 | Pea fiber | 78% | 62.0% | 2.00 |
| PPC81 | Wheat (WF200) | 85.2% | 63.6% | 2.70 |
| PPC89 | Wheat (WF 200) | ND | 64.5% | ND |
| PPC92 | Cellulose L00 | ND | 64.6% | ND |
| PPC91 | Pea fiber | ND | 64.5% | ND |
| PPC84 | Cellulose L700G | ND | 47.3% | ND |
| PPC89 | Wheat (WF 600) | 79% | 72% | 0.88 |

ND = not determined.

The release results show an increased release of nicotine after 10 min for pouches comprising fibers with a relative high water binding capacity, such as pea fibers, cellulose L700G and wheat fibers (WF200).

Example 10—Release Results

Pouches with pouch compositions similar to PPC46 were made, however, using the below indicated humectant, were exposed to the in vitro release experiment described in example 3L.

TABLE 18

Different humectants.

| Humectant | Remaining nicotine in pouch after 10 min |
|---|---|
| Modified starch | 68% |
| Glycerol | 71% |
| Alginate (PPC46) | 79% |

Example 11—Release Results

Pouches were exposed to the in vitro release experiment described in example 3L.

TABLE 19

In vitro release results.

| PPC | Weight % Fiber | Nicotine premix | Remaining nicotine in pouch after 10 min |
|---|---|---|---|
| PPC81 | 30 wt % Wheat (WF600) | II | 71.6% |
| PPC101 | 30 wt % Wheat (WF600) | VI | 66.6% |
| PPC88 | 15 wt % Wheat (WF600) | VI | 43.6% |
| PPC89 | 15 wt % Wheat (WF600) | II | 54.4% |
| PPC93 | 15 wt % Wheat (WF600) | VI | 34.6% |
| PPC94 | 15 wt % Wheat (WF600) | VI | 43.7% |
| PPC76 | 30 wt % peafiber | VI | 58.2% |
| PPC83 | 30 wt % peafiber | II | 62.0% |

ND = not determined.

Results demonstrate that release after 10 min is improved when using nicotine premix VI. The release can be further improved by including a buffer system, i.e. 3.5% sodium carbonate and 3.5% sodium bicarbonate (PPC93).

Also, the addition of 10% NaCl seems to improve the release obtained after 10 min (PPC94).

The invention claimed is:

1. A non-tobacco nicotine pouch composition, comprising:
   at least one sugar alcohol in an amount of from 10% to 40% by weight of the composition,
   at least one water-insoluble fiber in an amount of from 15% to 50% by weight of the composition,
   water in an amount of 15-45% by weight of the composition, and
   a nicotine in an amount of 0.1-5.0% by weight of the composition,
   wherein the pouch composition has a bulk density of from 0.25 g/cm$^3$ to 0.6 g/cm$^3$, and
   wherein the pouch composition comprises water and the at least one water-insoluble fiber in a weight ratio of 3.0:1.0 to 1.0:3.0.

2. The nicotine pouch composition according to claim 1, wherein the nicotine is selected from the group consisting of a nicotine salt, nicotine free base, nicotine bound to an ion exchanger, a nicotine inclusion complex, nicotine in any non-covalent binding, nicotine bound to zeolites, nicotine bound to cellulose, and mixtures thereof.

3. The nicotine pouch composition according to claim 1, wherein the nicotine comprises nicotine mixed with ion exchange resin.

4. The nicotine pouch composition according to claim 1, wherein the nicotine comprises a nicotine salt.

5. The nicotine pouch composition according to claim 1, wherein the nicotine comprises nicotine bound to an ion exchange resin.

6. The nicotine pouch composition according to claim 1, wherein the amount of nicotine is from 0.2 to 4.0% by weight of the pouch composition.

7. The nicotine pouch composition according to claim 1, wherein the pouch composition further comprises a basic pH-regulating agent.

8. The nicotine pouch composition according to claim 1, wherein the pouch composition comprises a pH regulating agent in an amount between 0.01 and 15% by weight of the pouch composition.

9. The nicotine pouch composition according to claim 3, wherein the pH regulating agent is a basic pH regulating agent selected from the group consisting of Sodium carbonate, Sodium bicarbonate, Potassium carbonate, Potassium bicarbonate, Magnesium carbonate, and any combination thereof.

10. The nicotine pouch composition according to claim 1, wherein the at least one sugar alcohol is selected from the group consisting of xylitol, maltitol, mannitol, erythritol, isomalt, sorbitol, lactitol, and mixtures thereof.

11. The nicotine pouch composition according to claim 1, wherein the water-insoluble fiber is selected from the group consisting of wheat fibers, pea fibers, rice fiber, maize fibers, oat fibers, tomato fibers, barley fibers, rye fibers, sugar beet fibers, buckwheat fibers, potato fibers, cellulose fibers, apple fibers, cocoa fibers, cellulose fibers, bran fibers, bamboo fibers, powdered cellulose, and combinations thereof.

12. The nicotine pouch composition according to claim 1, wherein the at least one water-insoluble fiber comprises or consists of water-insoluble fiber selected from the group consisting of wheat fibers, oat fibers, pea fibers, powdered cellulose, and combinations thereof.

13. The nicotine pouch composition according to claim 1, wherein the water-insoluble fiber has a water binding capacity of at least 200%.

14. The nicotine pouch composition according to claim 1, wherein the water-insoluble fiber has a density of 50 to 500 gram per Liter.

15. The nicotine pouch composition according to claim 1, wherein the pouch composition comprises the water and the at least one water-insoluble fiber in a weight ratio of no more than 2.5:1.

16. The nicotine pouch composition according to claim 1, wherein the pouch composition further comprises a humectant.

17. The nicotine pouch composition according to claim 1, wherein the pouch composition further comprises flavor in an amount of 0.01 and 20% by weight of the pouch composition.

18. An oral pouched nicotine product, comprising:
a saliva-permeable pouch and a non-tobacco nicotine pouch composition,
the nicotine pouch composition comprising:
at least one sugar alcohol in an amount of from 10% to 40% by weight of the composition,
at least one water-insoluble fiber in an amount of from 15% to 50% by weight of the composition,
water in an amount of 15-45% by weight of the composition, and
nicotine in an amount of 0.1-5.0% by weight of the composition,
wherein the composition does not comprise a triglyceride,
wherein the pouch composition has a bulk density of from 0.25 g/cm$^3$ to 0.6 g/cm$^3$, and
wherein the saliva permeable pouch has a maximum inner pouch volume and wherein the nicotine pouch composition has a volume corresponding to at least 65% of said maximum inner pouch volume.

19. The oral pouched nicotine product according to claim 18, wherein the maximum inner pouch volume is at least 0.5 mL.

20. The oral pouched nicotine product according to claim 18, wherein the at least one water-insoluble fiber has a water-solubility of less than 0.1 gram per 100 mL of water measured at 25 degrees Celsius and pH of 7.0.

21. The oral pouched nicotine product according to claim 18, wherein
the nicotine comprises 0.5-5.0% by weight of the composition,
the pouch composition comprises the water and the at least one water-insoluble fiber in a weight ratio of no more than 3.0:1.0 to 1.0:3.0, and
the at least one water-insoluble fiber has a water-solubility of less than 0.1 gram per 100 mL of water measured at 25 degrees Celsius and pH of 7.0.

22. A non-tobacco nicotine pouch, comprising:
at least one sugar alcohol in an amount of from 10% to 40% by weight of the composition,
at least one water-insoluble fiber in an amount of from 15% to 50% by weight of the composition,
water in an amount of 15-45% by weight of the composition, and
nicotine,
wherein the pouch composition has a bulk density of from 0.25 g/cm$^3$ to 0.6 g/cm, and
wherein the pouch composition is free of triglycerides.

* * * * *